(12) United States Patent
Navia

(10) Patent No.: US 8,216,303 B2
(45) Date of Patent: Jul. 10, 2012

(54) APPARATUS AND METHOD FOR TREATING A REGURGITANT HEART VALVE

(75) Inventor: Jose Luis Navia, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 53 days.

(21) Appl. No.: 12/274,087

(22) Filed: Nov. 19, 2008

(65) Prior Publication Data

US 2009/0132036 A1     May 21, 2009

Related U.S. Application Data

(60) Provisional application No. 60/988,825, filed on Nov. 19, 2007.

(51) Int. Cl.
*A61F 2/24*     (2006.01)
(52) U.S. Cl. ..................... 623/2.36; 623/1.26
(58) Field of Classification Search ............. 623/1.24, 623/1.26, 2.14, 2.18, 1.34, 1.36, 2.36–2.38; 606/151
See application file for complete search history.

(56) References Cited

U.S. PATENT DOCUMENTS

| | | | | |
|---|---|---|---|---|
| 5,360,444 | A * | 11/1994 | Kusuhara | 623/2.36 |
| 6,102,945 | A * | 8/2000 | Campbell | 623/2.37 |
| 6,143,024 | A * | 11/2000 | Campbell et al. | 623/2.36 |
| 6,187,040 | B1 * | 2/2001 | Wright | 623/2.36 |
| 6,231,602 | B1 * | 5/2001 | Carpentier et al. | 623/2.36 |
| 6,258,122 | B1 * | 7/2001 | Tweden et al. | 623/2.36 |
| 6,419,695 | B1 * | 7/2002 | Gabbay | 623/2.36 |
| 6,726,717 | B2 * | 4/2004 | Alfieri et al. | 623/2.36 |
| 6,749,630 | B2 * | 6/2004 | McCarthy et al. | 623/2.36 |
| 6,805,710 | B2 * | 10/2004 | Bolling et al. | 623/2.36 |
| 7,077,862 | B2 * | 7/2006 | Vidlund et al. | 623/2.36 |
| 7,220,277 | B2 * | 5/2007 | Arru et al. | 623/2.36 |

(Continued)

FOREIGN PATENT DOCUMENTS

WO     WO 99/04730 A1     2/1999

(Continued)

OTHER PUBLICATIONS

Boudjemline et al., "New Insights in Minimally Invasive Valve Replacement: Description of a Cooperative Approach for the Off-Pump Replacement of Mitral Valves", *European Heart Journal* 26 (2005) 2013-2017.

(Continued)

*Primary Examiner* — Alvin J Stewart
(74) *Attorney, Agent, or Firm* — Tarolli, Sundheim, Covell & Tummino LLP

(57) ABSTRACT

An apparatus is provided for treating regurgitation of blood flow through a diseased heart valve. The apparatus includes an annular support member and at least one posterior leaflet support member. The annular support member has an anterior end portion, a posterior end portion, and oppositely disposed first and second intermediate portions extending between the end portions. The at least one posterior leaflet support member is securely connected to the annular support member and is dimensioned to extend across a portion of a free edge of a posterior valve leaflet. The posterior leaflet support member comprises an arcuate center portion integrally formed with and extending between first and second end portions. The arcuate center portion has a concave shape relative to the anterior end portion. At least one of the first and second end portions is securely attached to the posterior end portion.

14 Claims, 21 Drawing Sheets

U.S. PATENT DOCUMENTS

| | | | |
|---|---|---|---|
| 7,294,148 B2 * | 11/2007 | McCarthy | 623/2.36 |
| 7,329,280 B2 * | 2/2008 | Bolling et al. | 623/2.36 |
| 7,367,991 B2 | 5/2008 | McCarthy et al. | |
| 7,381,220 B2 | 6/2008 | Macoviak et al. | |
| 7,527,646 B2 * | 5/2009 | Rahdert et al. | 623/2.36 |
| 7,608,103 B2 * | 10/2009 | McCarthy | 623/2.36 |
| 7,695,510 B2 * | 4/2010 | Bloom et al. | 623/2.36 |
| 7,695,511 B2 * | 4/2010 | Drake | 623/2.36 |
| 2003/0069593 A1 * | 4/2003 | Tremulis et al. | 606/142 |
| 2003/0199971 A1 | 10/2003 | Tower et al. | |
| 2004/0006384 A1 | 1/2004 | McCarthy | |
| 2004/0138745 A1 * | 7/2004 | Macoviak et al. | 623/2.36 |
| 2005/0004668 A1 * | 1/2005 | Aklog et al. | 623/2.36 |
| 2005/0010287 A1 * | 1/2005 | Macoviak et al. | 623/2.36 |
| 2005/0038508 A1 * | 2/2005 | Gabbay | 623/2.36 |
| 2005/0038509 A1 | 2/2005 | Ashe | |
| 2006/0052868 A1 * | 3/2006 | Mortier et al. | 623/2.36 |
| 2006/0069430 A9 * | 3/2006 | Rahdert et al. | 623/2.36 |
| 2006/0229708 A1 | 10/2006 | Powell et al. | |
| 2006/0247492 A1 | 11/2006 | Streeter | |
| 2007/0050020 A1 | 3/2007 | Spence | |
| 2008/0097593 A1 * | 4/2008 | Bolling et al. | 623/2.36 |

FOREIGN PATENT DOCUMENTS

WO   WO 2007/072399 A1   6/2007

OTHER PUBLICATIONS

Walther et al., "Valve-in-a-Valve Concept for Transcatheter Minimally Invasive Repeat Xenograft Implantation", *Journal of the American College of Cardiology* 50 (2007) 56-60.

Ma et al., "Double-Crowned Valved Stents for Off-Pump Mitral Valve Replacement", *European Journal of Cardio-Thoracic Surgery* 28 (2005) 194-199.

Lozonschi et al., "Transapical Mitral Valved Stent Implantation", *Ann Thorac Surgery* 86 (2008) 745-748.

\* cited by examiner

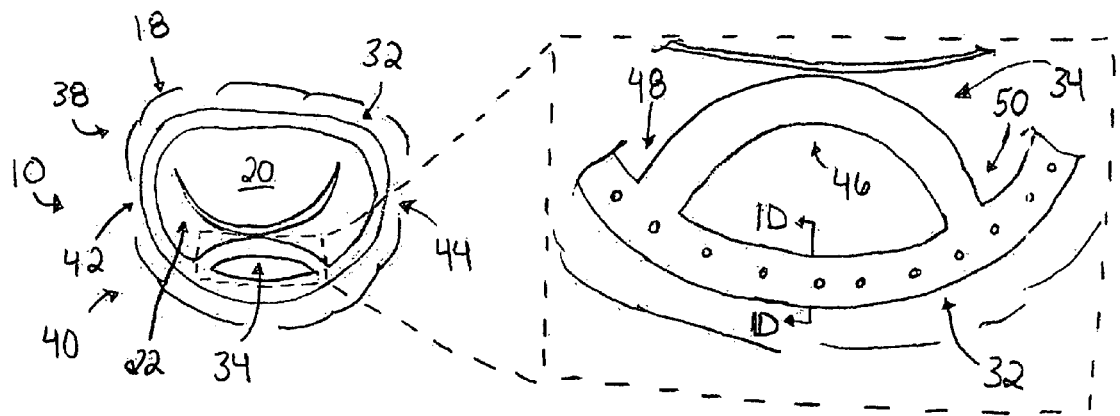
Fig. 1A
Fig. 1B
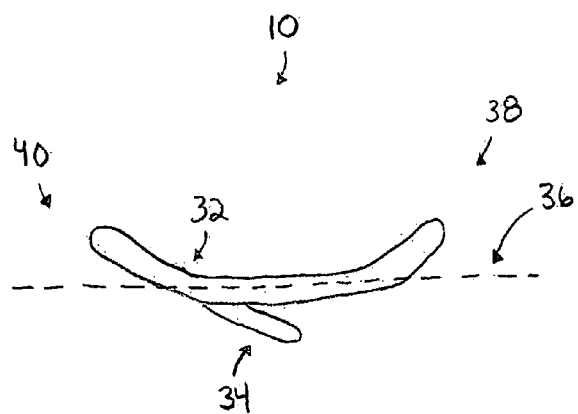
Fig. 1C

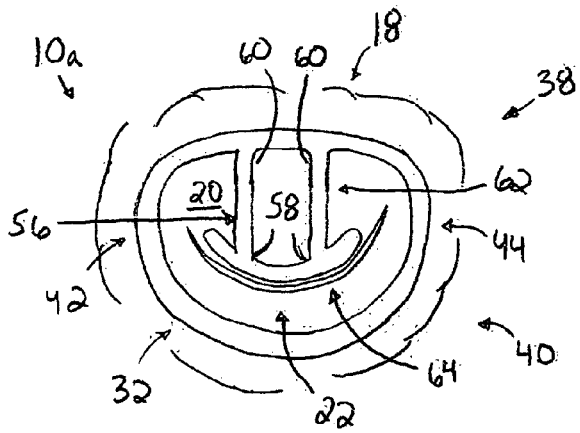
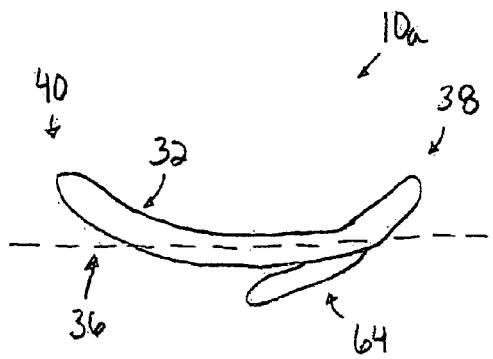
Fig. 10A
Fig. 10B
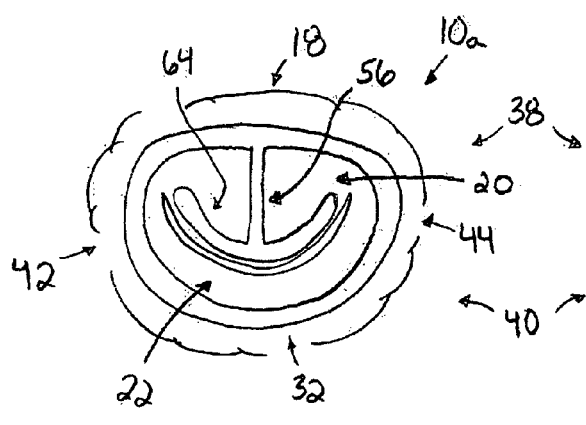
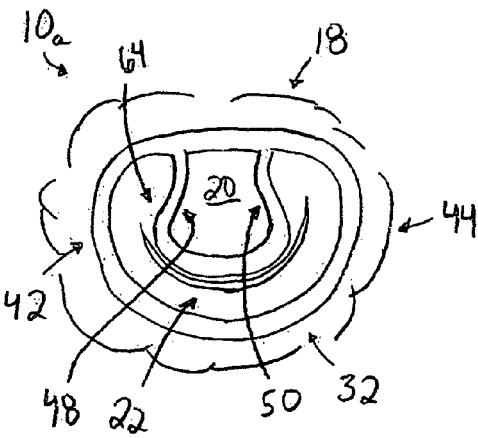
Fig. 11
Fig. 12

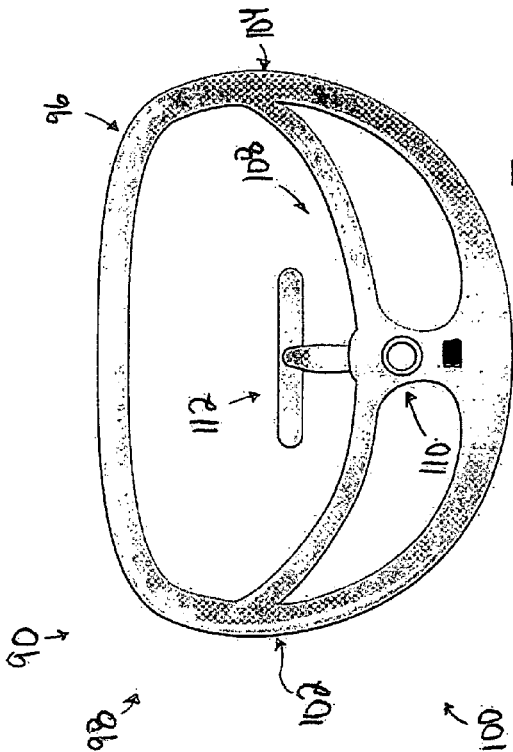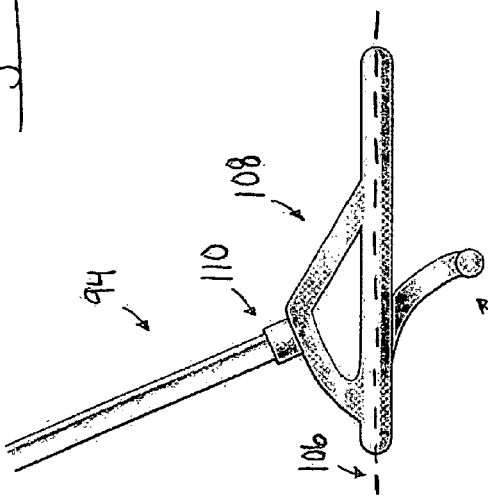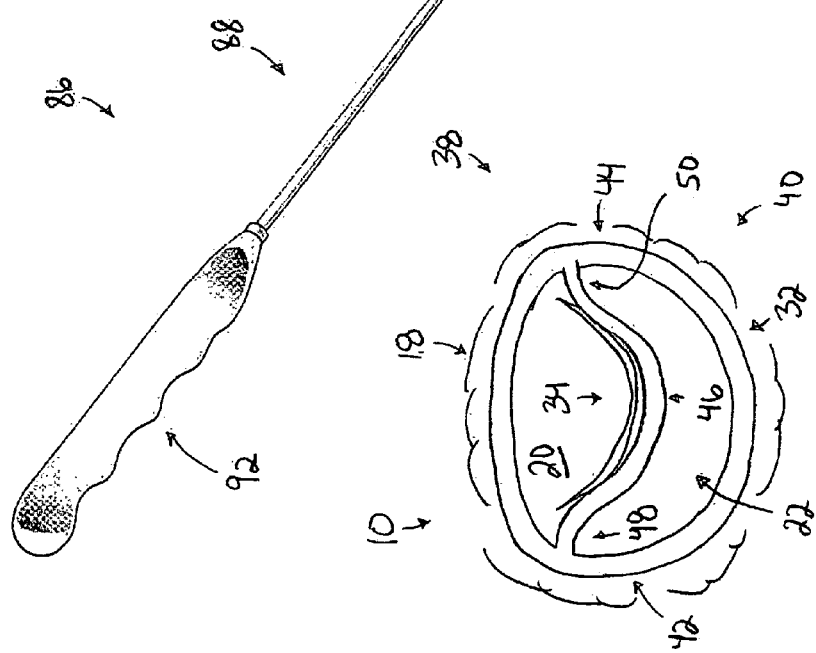

APPARATUS AND METHOD FOR TREATING A REGURGITANT HEART VALVE

RELATED APPLICATION

This application claims priority from U.S. Provisional Application No. 60/988,825, filed Nov. 19, 2007, the subject matter of which is incorporated herein by reference.

TECHNICAL FIELD

The present invention relates generally to apparatus and methods for treating dysfunctional heart valves, and more particularly to apparatus and related methods that passively assist in preventing or mitigating heart valve prolapse.

BACKGROUND OF THE INVENTION

The opening and closing of heart valves occur primarily as a result of pressure differences. For example, the opening and closing of the mitral valve occurs as a result of the pressure differences between the left atrium and the left ventricle. During ventricular diastole, the venous return of blood from the pulmonary veins into the left atrium causes the pressure in the atrium to exceed that in the left ventricle. As a result, the mitral valve opens and allows blood to enter the left ventricle. As the left ventricle contracts during ventricular systole, the intraventricular pressure rises above the pressure in the atrium and pushes the mitral valve shut.

When the high pressure produced by contraction of the left ventricle pushes the valve leaflets too much, the leaflets become everted and prolapse results. This is normally prevented by contraction of the papillary muscles within the left ventricle, which are connected to the mitral valve leaflets by the chordae tendineae (chords). Contraction of the papillary muscles is simultaneous with the contraction of the left ventricle and serves to keep healthy mitral valve leaflets tightly shut at peak contraction pressures.

Mitral valve malfunction can result from the chords becoming stretched and, in some cases, tearing. When a chord tears, for example, the result is a flailed or prolapsed leaflet. Also, a normally-structured valve may not function properly because of an enlargement of the valve annulus. This condition is referred to as a dilation of the annulus, and generally results from heart muscle failure. In addition, the valve may be defective at birth or because of an acquired disease.

SUMMARY OF THE INVENTION

According to one aspect of the present invention, an apparatus is provided for treating regurgitation of blood flow through a diseased heart valve. The diseased heart valve includes an annulus, an anterior valve leaflet, and a posterior valve leaflet. Each of the anterior and posterior valve leaflets has a free edge. The apparatus comprises an annular support member and at least one posterior leaflet support member. The annular support member has an anterior end portion, a posterior end portion, and oppositely disposed first and second intermediate portions extending between the anterior and posterior end portions. The annular support member is dimensioned for attachment to the annulus of the heart valve. The at least one posterior leaflet support member is securely connected to the annular support member and is dimensioned to extend across a portion of the free edge of the posterior valve leaflet. The posterior leaflet support member comprises an arcuate center portion integrally formed with and extending between first and second end portions. The arcuate center portion has a concave shape relative to the anterior end portion. At least one of the first and second end portions is securely attached to the posterior end portion.

According to another aspect of the present invention, an apparatus is provided for treating regurgitation of blood flow through a diseased heart valve. The diseased heart valve includes an annulus, an anterior valve leaflet, and a posterior valve leaflet. Each of the anterior and posterior valve leaflets has a free edge. The apparatus comprises, at least one posterior leaflet support member, and at least one anterior support member. The annular support member has an anterior end portion, a posterior end portion, and oppositely disposed first and second intermediate portions extending between the anterior and posterior end portions. The annular support member is dimensioned for attachment to the annulus of the heart valve. The at least one posterior leaflet support member is securely connected to the annular support member and is dimensioned to extend across a portion of the free edge of the posterior valve leaflet. The posterior leaflet support member comprises a first arcuate center portion integrally formed with and extending between first and second end portions. The first arcuate center portion has a concave shape relative to the anterior end portion. Each of the first and second end portions has a convex shape relative to the anterior end portion, and is securely attached to the posterior end portion at oppositely disposed locations. The at least one anterior leaflet support member is securely connected to the annular support member, and is dimensioned to extend across a portion of the free edge of the anterior valve leaflet. The anterior leaflet support member comprises a second arcuate center portion integrally formed with and extending between third and fourth end portions. The second arcuate center portion has a convex shape relative to the anterior end portion. Each of the third and fourth end portions has a concave shape relative to the anterior end portion, and is securely attached to the first and second intermediate portions, respectively.

According to another aspect of the present invention, an apparatus is provided for treating regurgitation of blood flow through a diseased heart valve. The diseased heart valve includes an annulus, an anterior valve leaflet, and a posterior valve leaflet. Each of the anterior and posterior valve leaflets has a free edge. The apparatus comprises an annular support member, at least one posterior leaflet support member, and at least one anterior leaflet support member. The annular support member has an anterior end portion, a posterior end portion, and oppositely disposed first and second intermediate portions extending between the anterior and posterior end portions. The annular support member is dimensioned for attachment to the annulus of the heart valve. The at least one posterior leaflet support member is securely connected to the annular support member, and is dimensioned to extend across a portion of the free edge of the posterior valve leaflet. The at least one posterior leaflet support member comprises a first arcuate center portion integrally formed with and extending between first and second end portions. The first arcuate center portion has a convex shape relative to the anterior end portion. Each of the first and second end portions is securely attached to the posterior end portion at oppositely disposed locations. The at least one anterior leaflet support member is securely connected to the annular support member and is dimensioned to extend across a portion of the free edge of the anterior valve leaflet. The anterior leaflet support member comprises a second arcuate center portion integrally formed with and extending between third and fourth end portions. The second arcuate center portion has a convex shape relative to the anterior end portion. Each of the third and fourth end portions is securely attached to oppositely disposed locations about the annular support member.

According to another aspect of the present invention, an apparatus is provided for treating regurgitation of blood flow through a diseased heart valve. The diseased heart valve includes an annulus, an anterior valve leaflet, and a posterior valve leaflet. Each of the anterior and posterior valve leaflets has a free edge. The apparatus comprises an annular support member, at least one posterior leaflet support member, and at least one anterior leaflet support member. The annular support member has an anterior end portion, a posterior end portion, and oppositely disposed first and second intermediate portions extending between the anterior and posterior end portions. The annular support member is dimensioned for attachment to the annulus of the heart valve. The at least one posterior leaflet support member is securely connected to the annular support member and is dimensioned to extend across a portion of the free edge of the posterior valve leaflet. The posterior leaflet support member comprises a first arcuate center portion integrally formed with and extending between first and second end portions. The first arcuate center portion has a concave shape relative to the anterior end portion. Each of the first and second end portions is securely attached to the annular support member at oppositely disposed locations. The at least one anterior leaflet support member is securely connected to the annular support member and is dimensioned to extend across a portion of the free edge of the anterior valve leaflet. The anterior leaflet support member comprises a second arcuate center portion integrally formed with and extending between third and fourth end portions. The second arcuate center portion has a convex shape relative to the anterior end portion. Each of the third and fourth end portions is securely attached to the annular support member at oppositely disposed locations. The first and second arcuate center portions are joined together to form a common junction. The common junction supports a portion of each of the free edges of the anterior and posterior valve leaflets.

According to another aspect of the present invention, a sizing device comprises a handle member connected to a sizing member. The handle member includes a handle fluidly connected to a distal attachment portion. The sizing member is securely attached to the distal attachment portion. The sizing member defines a longitudinal axis and includes an annular member having an anterior end portion, a posterior end portion, and first and second intermediate portions extending between the anterior and posterior end portions. The sizing member further includes a bracing portion that extends between the first and second intermediate portions and a leaflet support member connected thereto. The leaflet support member extends below the longitudinal axis.

According to another aspect of the present invention, a method is provided for treating regurgitation of blood flow through a diseased heart valve. The diseased heart valve includes an annulus, an anterior valve leaflet, and a posterior valve leaflet. Each of the anterior and posterior valve leaflets has a free edge. One step of the method comprises providing an apparatus including an annular support member and at least one leaflet support member securely connected to the annular support member. The annular support member comprises an anterior end portion, a posterior end portion, and oppositely disposed first and second intermediate portions extending between the anterior and posterior end portions. The at least one leaflet support member comprises a first end portion, a second end portion, and an arcuate center portion extending between the first and second end portions. The arcuate center portion has a convex shape relative to the anterior end portion. Next, the annular support member is attached to the annulus of the diseased heart valve so that at least one free edge of the anterior and posterior valve leaflets coapts with a portion of the at least one leaflet support member to prevent or substantially reduce regurgitation of blood flow through the diseased heart valve.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1A is a top view of an apparatus for treating regurgitation of blood flow through a diseased heart valve constructed according to one embodiment of the present invention;

FIG. 1B is an exploded view of the apparatus shown in FIG. 1A;

FIG. 1C is a side view of the apparatus in FIG. 1A;

FIG. 10A is a plan view showing an alternative embodiment of the apparatus in FIG. 1A;

FIG. 10B is a side view of the apparatus in FIG. 10A;

FIG. 11 is a plan view showing an alternative embodiment of the apparatus in FIG. 10A;

FIG. 12 is a plan view showing an alternative embodiment of the apparatus in FIG. 10A;

FIG. 32 is a plan view showing an alternative embodiment of the apparatus in FIG. 1A;

FIG. 33A is a perspective view showing a sizing device comprising a handle member fluidly attached to a sizing member;

FIG. 33B is a top view showing the sizing member in FIG. 33A;

FIG. 33C is a side view showing a portion of the handle member and the sizing member in FIG. 33A;

DETAILED DESCRIPTION

Figure 1D:
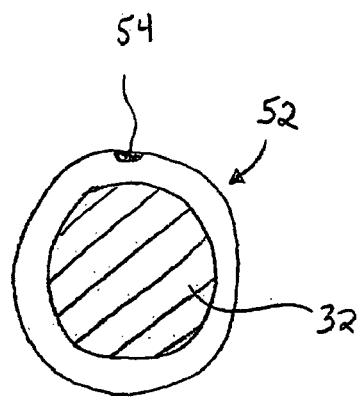
FIG. 1D is a cross-sectional view taken along Line 1D-1D in FIG. 1B.
Figure 1E:
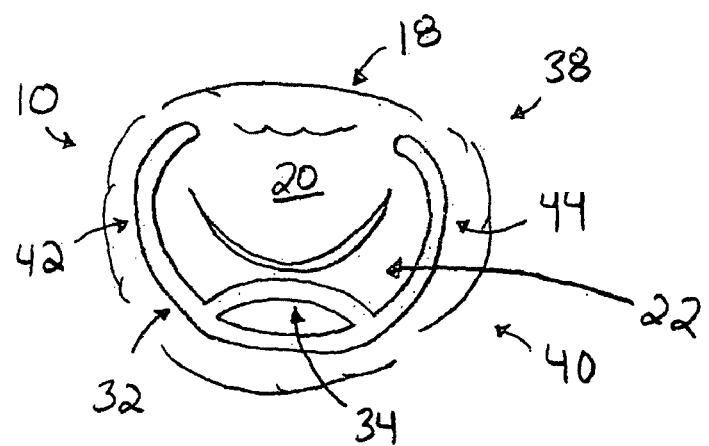
FIG. 1E is a top view showing an alternative embodiment of the apparatus in FIG. 1A.

The present invention relates generally to apparatus and methods for treating dysfunctional heart valves, and more particularly to apparatus and related methods that passively assist in preventing or mitigating heart valve prolapse. As representative of the present invention, FIGS. 1A-E illustrate an apparatus 10 for treating regurgitation of blood flow through a diseased heart valve, such as a mitral valve 12 (FIG. 2). It should be appreciated that although the present invention is described herein as being used to treat mitral regurgitation through a diseased mitral valve 12, the apparatus 10 can also be used to treat other cardiac valves, such as the tricuspid valve (not shown).

As shown in FIG. 2, the mitral valve 12 is located between the left atrium 14 and the left ventricle 16, and functions to prevent the backflow of blood from the left ventricle into the left atrium during contraction. The mitral valve 12 has a D-shaped annulus 18 that defines the opening between the left atrium 14 and the left ventricle 16. The mitral valve 12 is formed by two leaflets; namely, the anterior leaflet 20 and the posterior leaflet 22. The anterior leaflet 20 extends along the generally planar base of the D-shaped valve annulus 18 between two fibrous trigones (not shown). The posterior leaflet 22 extends arcuately around the curved portion of the D-shaped annulus 18 of the mitral valve 12. Chordae tendineae 24 extend between the free edge 26 of the anterior mitral leaflet 20 and the free edge 28 of the posterior mitral leaflet 22 to the papillary muscles 30 in the left ventricle 16.

Figure 2:
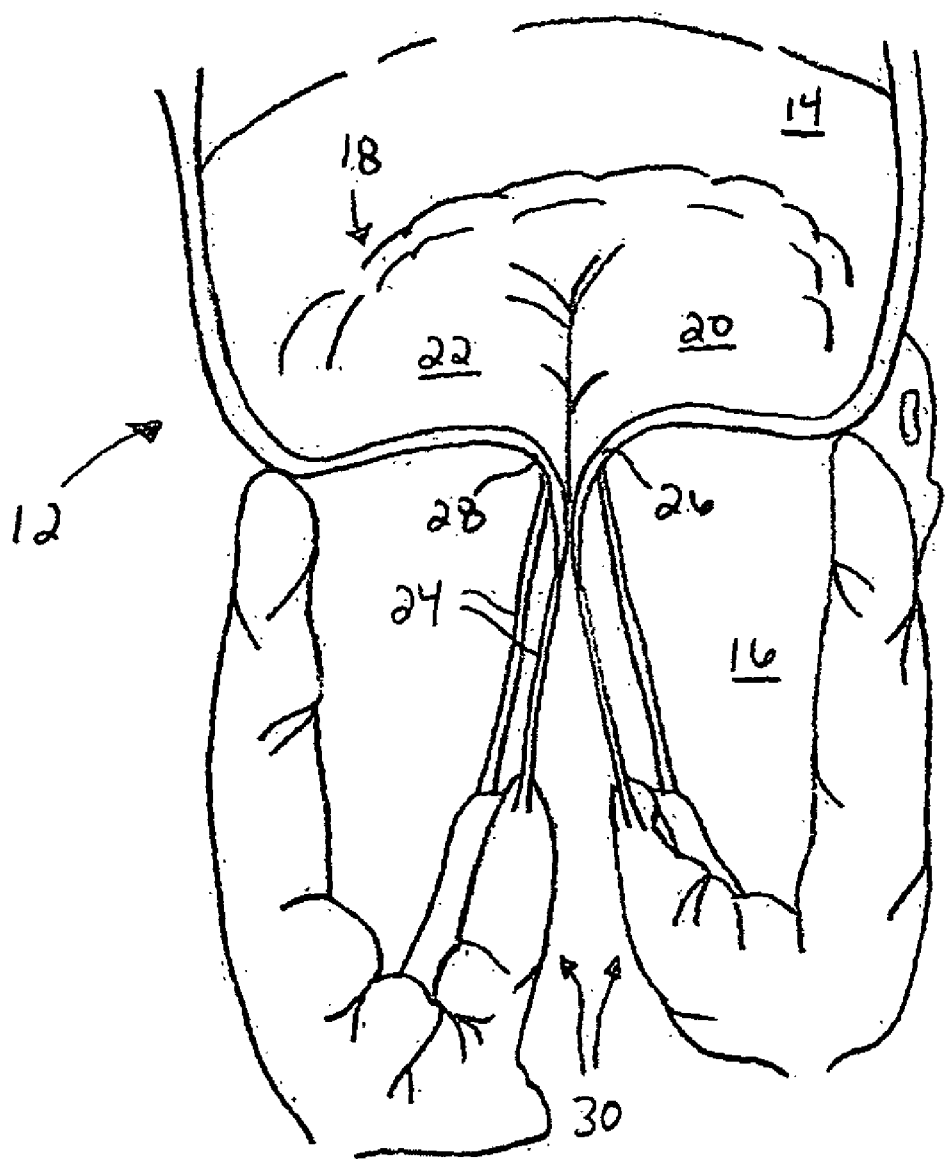
FIG. 2 is a cross-sectional view showing the left side of a human heart.

One embodiment of the present invention is illustrated in FIGS. 1A-E. As shown in FIGS. 1A-B, an apparatus 10 for treating regurgitation of blood flow through a mitral valve 12 comprises an annular support member 32 and at least one posterior leaflet support member 34 securely connected thereto. The apparatus 10 has a three-dimensional (3D) shape that corresponds to the saddle-like shape of the mitral annulus 18 (FIG. 1C). The 3D shape allows the apparatus 10 to complement the 3D shape of the mitral valve 12 during the complex physiological motion associated with the cardiac cycle. This removes the need for leaflet resection and/or annulus plication because the apparatus 10, when implanted in the mitral valve 12, passively assists in providing leaflet support without becoming deformed during the cardiac cycle.

Referring to FIG. 1A, the apparatus 10 comprises an annular support member 32 that defines a longitudinal axis 36 (FIG. 1C) and includes an anterior end portion 38 (FIG. 1A), a posterior end portion 40, and oppositely disposed first and second intermediate portions 42 and 44 extending between the anterior and posterior end portions. As noted, the annular support member 32 has a D-shaped configuration that corresponds to the D-shaped mitral valve annulus 18. It should be appreciated, however, that the annular support member 32 may have other configurations, such as a U- or C-shaped configuration (FIG. 1E) for conforming to a portion of the mitral valve annulus 18.

The posterior leaflet support member 34 is dimensioned to extend across a portion of the free edge 28 of the posterior mitral leaflet 22. For example, the posterior leaflet support member 34 can extend across the entire free edge 28 of the posterior valve leaflet 22, or only a portion thereof. The shape of the posterior leaflet support member 34 mirrors the 3D shape of the posterior mitral leaflet 22 and the free edge 28 to facilitate optimal leaflet coaptation with the posterior leaflet support member. For example, the posterior leaflet support member 34 supports the free edge 28 of the posterior mitral leaflet 22 during systole to prevent or mitigate prolapse of the posterior mitral leaflet and thereby prevent or mitigate regurgitation of blood flow through the mitral valve 12.

The posterior leaflet support member 34 can have a rigid or semi-rigid configuration. Where the posterior leaflet support member 34 has a semi-rigid configuration, for example, the posterior leaflet support member can be bendable or adjustable to various positions. The posterior leaflet support member 34 can also include an adjustment mechanism (not shown) for selectively adjusting the position of the posterior leaflet support member relative to the annular support member 32. As shown in FIG. 1C, the posterior leaflet support member 34 can extend below the longitudinal axis 36 of the annular support member 32. The orientation of the posterior leaflet support member 34 below the longitudinal axis 36 facilitates proper coaptation of the free edge 28 of the posterior mitral leaflet 22 with the posterior leaflet support member to prevent or mitigate regurgitation of blood flow through the mitral valve 12.

Figure 3A:
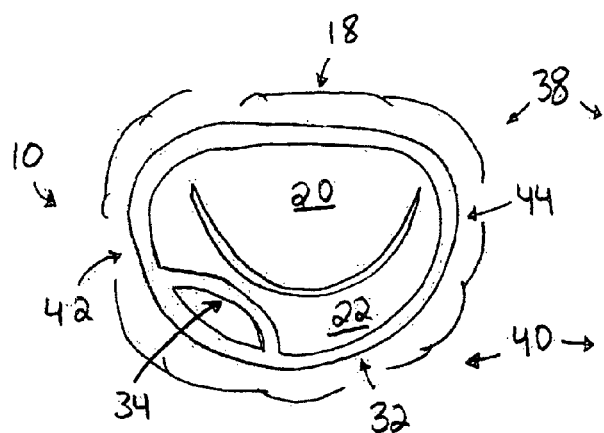
FIG. 3A is a plan view showing an alternative embodiment of the apparatus in FIG. 1A.

The at least one posterior leaflet support member 34 has an elongated, U-shaped configuration and comprises an arcuate center portion 46 integrally formed with an extending between first and second end portions 48 and 50. The arcuate center portion 46 has a concave shape relative to the anterior end portion 38 of the annular support member 32. Although the apparatus 10 in FIGS. 1A-E is shown as comprising only one posterior leaflet support member 34, it should be appreciated that the apparatus can include two (FIG. 3C), three, four, or even more posterior leaflet support members.

Figure 3B:
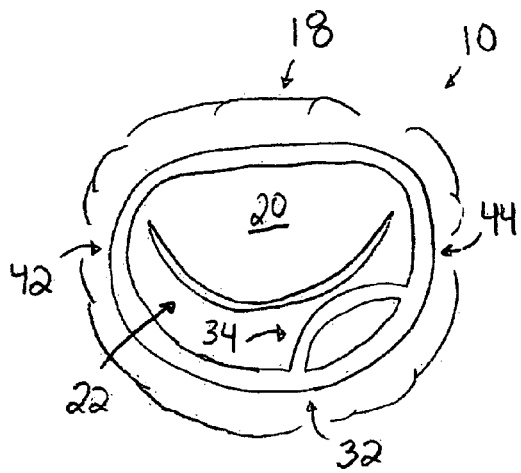
FIG. 3B is a plan view showing an alternative embodiment of the apparatus in FIG. 1A.
Figure 3C:
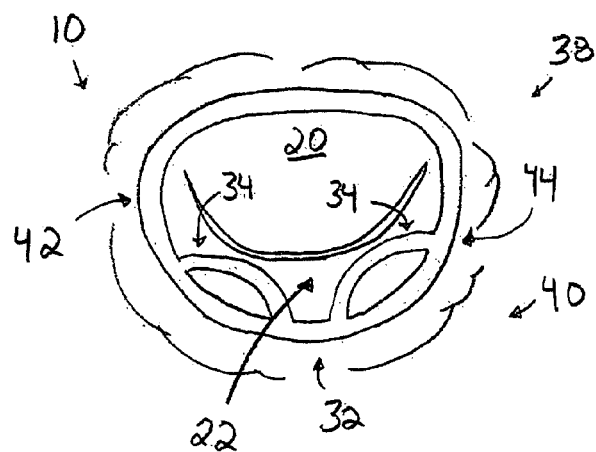
FIG. 3C is a plan view showing an alternative embodiment of the apparatus in FIG. 1A.

At least one of the first and second end portions 48 and 50 (FIG. 1B) is securely attached to the posterior end portion 40 of the annular support member 32. The first and second end portions 48 and 50 can be integrally formed with the annular support member 32 or, alternatively, securely connected thereto using sutures, clips, or some other sort of snap-fit mechanism (not shown). As shown in FIGS. 1A-B, each of the first and second end portions 48 and 50 is securely connected to the posterior end portion 40 at oppositely disposed locations. Alternatively, the first and second end portions 48 and 50 can be connected to the first intermediate portion 42 and the posterior end portion 40, respectively (FIG. 3A); or, as shown in FIG. 3B, the first and second end portions can be connected to the posterior end portion and the second intermediate portion 44, respectively.

The apparatus 10 can be made of any rigid or semi-rigid material that allows manual deformation, and yet is rigid enough to withstand further deformation once implanted (i.e., when subject to normal physiological stresses). Non-limiting examples of materials for constructing the apparatus 10 can include biocompatible, medical grade metals, such as metal alloys, plastics, Nitinol, stainless steel, titanium, pyrrolitic carbon, and the like.

All or only a portion of the apparatus 10 can be covered with a layer 52 of biocompatible material (FIG. 1D). The layer 52 of biocompatible material can comprise a synthetic material, such as DACRON, woven velour, polyurethane, PTFE, ePTFE, or heparin-coated fabric. Alternatively, the layer 52 can comprise a biological material, such as bovine or equine pericardium, a homograft, patient graft, or a cell-seeded tissue. The layer 52 can cover the inside surface of the annular support member 32, the outside surface of the annular support member, or can be wrapped around both the inside and outside surfaces. As shown in FIG. 1D, for example, the layer 52 may be attached around the entire circumference of the annular support member 32. It should be appreciated that the layer 52 can cover any portion of the apparatus 10. As shown in FIG. 1B and FIG. 1D, the layer 52 includes a plurality of markers 54 to facilitate attachment of the apparatus 10 to the mitral annulus 18. The markers 54 can include pre-formed holes to facilitate suture placement, for example, or, alternatively, color indicia (not shown) to indicate where sutures should be placed to stabilize of the apparatus 10 in vivo. It should be appreciated that a portion of the apparatus 10 can be enlarged or reinforced at the level of the trigones (not shown) to facilitate implantation and leaflet coaptation by including additional biocompatible layers about the desired portion(s).

At least a portion of the apparatus 10 can be treated with one or a combination of therapeutic agents capable of eluting into a cardiac chamber and/or a cardiac tissue. The therapeutic agent can be capable of preventing a variety of pathological conditions including, but not limited to, arrhythmias, thrombosis, stenosis, apoptosis, and inflammation. Accordingly, the therapeutic agent may include at least one of an anti-arrhythmic agent, anticoagulant, an antioxidant, a fibrinolytic, a steroid, an anti-apoptotic agent, an anti-overgrowth agent (i.e., capable of preventing epithelial cell overgrowth), and/or an anti-inflammatory agent. Optionally or additionally, the therapeutic agent may be capable of treating or preventing other disease or disease processes, such as microbial infections and heart failure. In these instances, the therapeutic agent may include an anti-microbial agent, an inotropic agent, a chronotropic agent, and/or a biological agent, such as a cell or protein.

Figure 4:
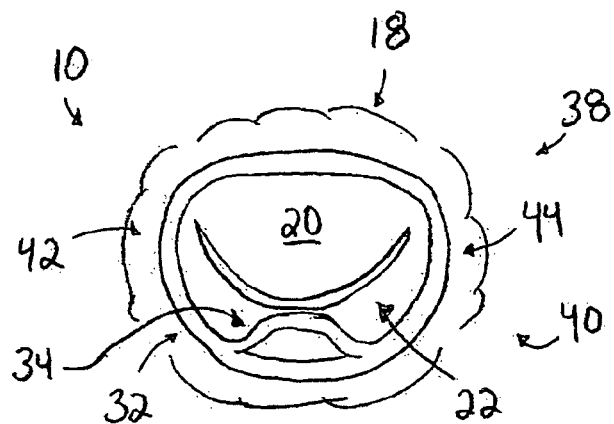
FIG. 4 is a plan view showing an alternative embodiment of the apparatus in FIG. 1A.

FIGS. 4-9 illustrate other geometric variations of the apparatus 10 shown in FIGS. 1A-E. As shown in FIG. 4, for example, the posterior leaflet support member 34 can alternatively comprise an arcuate center portion 46 integrally formed with first and second end portions 48 and 50. The first and second end portions 48 and 50 can have a convex shape relative to the anterior end portion 38 of the annular support member 32. Each of the first and second end portions 48 and 50 can be attached to the posterior end portion 40 of the annular support member 32 at oppositely disposed locations. The arcuate center portion 46 of the posterior leaflet support member 34 can have a concave shape relative to the anterior end portion 38, and can extend across a portion of the free edge 28 of the posterior mitral leaflet 22.

Figure 5:
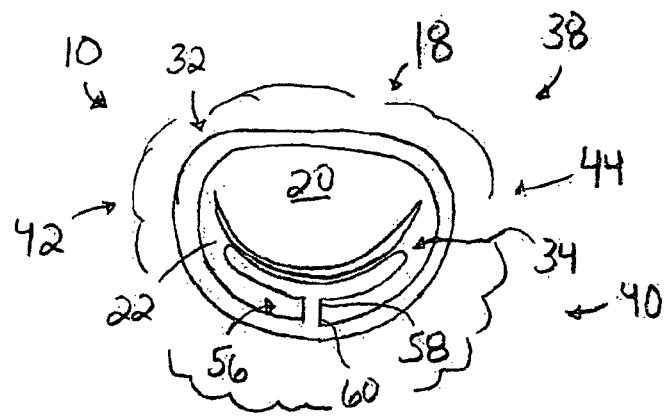
FIG. 5 is a plan view showing an alternative embodiment of the apparatus in FIG. 1A.

As shown in FIG. 5, the posterior leaflet support member 34 can alternatively comprise an arcuate center portion 46 integrally formed with and extending between first and second end portions 48 and 50. The arcuate center portion 34 can be integrally formed with a first brace member 56 having first and second ends 58 and 60. More particularly, the first end 58 can be securely connected to the arcuate center portion 46, and the second end 60 can be securely connected to the posterior end portion 40 of the annular support member 32. The arcuate center portion 46 can have a convex shape relative to the anterior end portion 38 of the annular support member 32, and can extend across a portion of the free edge 28 of the posterior mitral leaflet 22.

Figure 6:
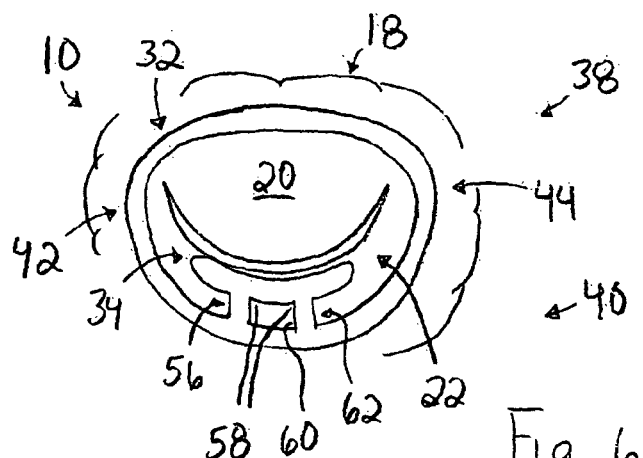
FIG. 6 is a plan view showing an alternative embodiment of the apparatus in FIG. 1A.

As shown in FIG. 6, the posterior leaflet support member 34 can alternatively comprise an arcuate center portion 46 integrally formed with and extending between first and second end portions 48 and 50. The arcuate center portion 46 can be integrally formed with first and second brace members 56 and 62. More particularly, each of the first and second brace members 56 and 62 can include first and second ends 58 and 60 that are respectively connected to the arcuate center portion 46 and the posterior end portion 40 of the annular support member 32. The arcuate center portion 46 can have a convex shape relative to the anterior end portion 38 of the annular support member 32, and can extend across a portion of the free edge 28 of the posterior mitral leaflet 22.

Figures 7, 8:
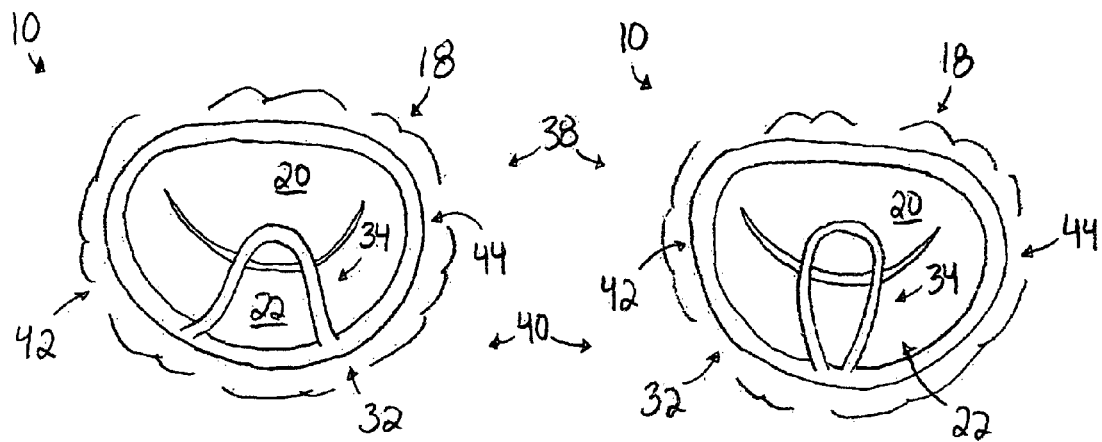
FIG. 7 is a plan view showing an alternative embodiment of the apparatus in FIG. 1A.
FIG. 8 is a plan view showing an alternative embodiment of the apparatus in FIG. 7.
Figure 9:
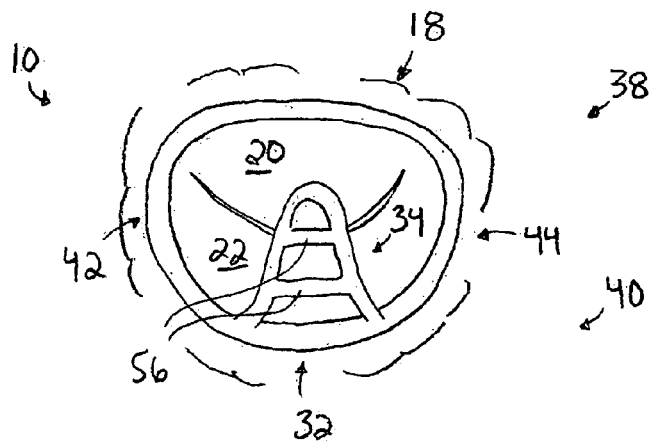
FIG. 9 is a plan view showing an alternative embodiment of the apparatus in FIG. 8.

It should be appreciated that the posterior leaflet support member 34 can extend across a portion of the free edges 28 and 26 of the posterior and anterior mitral leaflets 22 and 20. As shown in FIGS. 7-9, for example, the arcuate center portion 46 of the posterior leaflet support member 34 can extend across a portion of the anterior mitral leaflet 20, while the first and second end portions 48 and 50 extend across a portion of the free edges 26 and 28 of the posterior mitral leaflet 22 and the anterior mitral leaflet. The posterior leaflet support member 34 can also include at least one brace member 56 extending substantially perpendicular to the first and second end portions 48 and 50. As shown in FIG. 9, for example, the brace member 56 can provide additional support for the posterior mitral leaflet 22 and/or the anterior mitral leaflet 20.

Another embodiment of the present invention is illustrated in FIGS. 10A-B. The apparatus $10_a$ shown in FIGS. 10A-B is identically constructed as the apparatus 10 shown in FIGS. 1A-E, except as described below. In FIGS. 10A-B, structures that are identical as structures in FIGS. 1A-E use the same reference numbers, whereas structures that are similar but not identical carry the suffix "a". It should be appreciated that the apparatus $10_a$ can be constructed from any of the materials described above, and that the apparatus can include a layer 52 of biocompatible material and/or a therapeutic agent(s), as also described above.

As shown in FIGS. 10A-B, the apparatus $10_a$ can comprise an annular support member 32 and at least one anterior leaflet support member 64 securely connected thereto. The apparatus $10_a$ can have a 3D shape that corresponds to the saddle-like shape of the mitral annulus 18 (FIG. 10B). The annular support member 32 can define a longitudinal axis 36 and include an anterior end portion 38 (FIG. 10A), a posterior end portion 40, and oppositely disposed first and second intermediate portions 42 and 44 extending between the anterior and posterior end portions. It should be appreciated that the annular support member 32 can have other configurations, such as a U- or C-shaped configuration.

The anterior leaflet support member 64 can be dimensioned to extend across a portion of the free edge 26 of the anterior mitral leaflet 20. For example, the anterior leaflet support member 64 can extend across the entire free edge 26, or only a portion of the anterior mitral leaflet 20. The shape of the anterior leaflet support member 64 can mirror the 3D shape of the anterior mitral leaflet 20 and the free edge 26 to facilitate optimal leaflet coaptation with the anterior leaflet support member. For example, the anterior leaflet support member 64 can support the free edge 26 of the anterior mitral leaflet 20 during systole to prevent or mitigate prolapse of the anterior mitral leaflet and thereby prevent or mitigate regurgitation of blood flow through the mitral valve 12.

The anterior leaflet support member 64 can have a rigid or semi-rigid configuration. Where the anterior leaflet support member 64 has a semi-rigid configuration, the anterior leaflet support member can be bendable or adjustable to various positions. The anterior leaflet support member 64 can also include an adjustment mechanism (not shown) for selectively adjusting the position of the anterior leaflet support member relative to the annular support member 32. As shown in FIG. 10B, the anterior leaflet support member 64 can extend below the longitudinal axis 36 of the annular support member 32. The orientation of the anterior leaflet support member 64 below the longitudinal axis 36 facilitates proper coaptation of the free edge 26 of the anterior mitral leaflet 20 with the anterior leaflet support member to prevent or mitigate regurgitation of blood flow through the mitral valve 12.

The anterior leaflet support member 64 can have an anchor-like configuration and comprise an arcuate center portion 46 integrally formed with an extending substantially perpendicular to first and second brace members 56 and 62. The arcuate center portion 46 has a convex shape relative to the anterior end portion 38 of the annular support member 32. Each of the first and second brace members 56 and 62 can include a first end 58 a second end 60. The first end 58 of the first brace member 56 and the first end of the second brace member 62 can each be connected to the arcuate center portion 46. Additionally, the second end 60 of the first brace member 56 and the second end of the second brace member 62 can each be connected to the anterior end portion 38 of the annular support member 32. The first and second brace members 56 and 62 can be integrally formed with both the annular support member 32 and the arcuate center portion 46. Alternatively, the first and second brace members 56 and 62 can be securely connected to both the anterior end portion 38 and the arcuate center portion 46 using sutures, clips, or some other sort of snap-fit mechanism (not shown). Although the apparatus $10_a$ in FIG. 10A is shown as comprising only one anterior leaflet support member 64, it should be appreciated that the apparatus can include two, three, four, or even more posterior leaflet support members.

Figure 13:
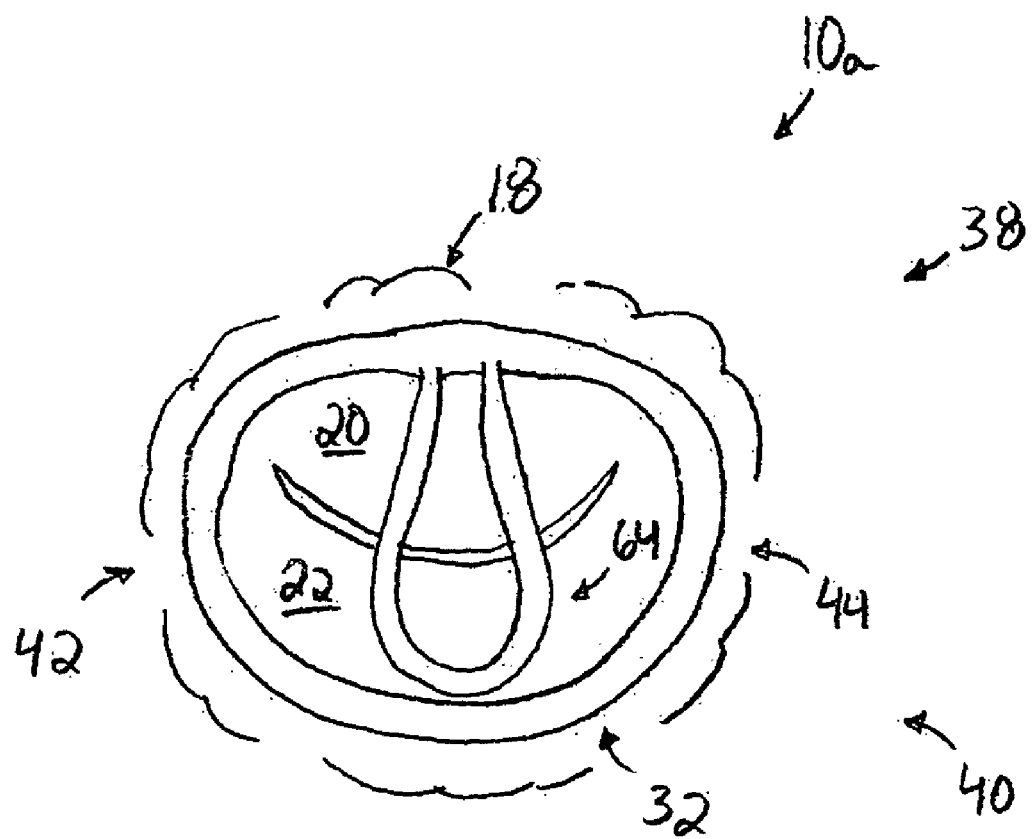
FIG. 13 is a plan view showing an alternative embodiment of the apparatus in FIG. 10A.

FIGS. 11-13 illustrate other geometric variations of the apparatus $10_a$ shown in FIGS. 10A-B. As shown in FIG. 11, for example, the apparatus $10_a$ can alternatively include an anterior leaflet support member 64 comprising an arcuate center portion 46 integrally formed with a first brace member 56 having a first end 58 and a second end 60. The first end 58 of the first brace member 56 can be integrally formed with the arcuate center portion 46, and the second end 60 can be integrally formed with the anterior end portion 38 of the annular support member 32. The arcuate center portion 46 can have a convex shape relative to the anterior end portion 38, and can extend across a portion of the free edge 26 of the anterior leaflet 20.

As shown in FIG. 12, the apparatus $10_a$ can include an anterior leaflet support member 64 alternatively comprising an arcuate center portion 46 integrally formed with and extending between first and second end portions 48 and 50. The arcuate center portion 46 can have a convex shape relative to the anterior end portion 38 of the annular support member 32. Additionally, each of the first and second end portions 48 and 50 can have a convex shape relative to the first and second intermediate portions 42 and 44, respectively. The first and second end portions 48 and 50 can be securely connected to the anterior end portion 38 of the annular support member 32 at oppositely disposed locations.

It should be appreciated that the anterior leaflet support member 64 can extend across a portion of the free edges 28 and 26 of the posterior and anterior mitral leaflets 22 and 20. As shown in FIG. 13, for example, the arcuate center portion 46 of the anterior leaflet support member 64 can extend across a portion of the posterior mitral leaflet 22. Additionally, each of the first and second end portions 48 and 50 of the anterior leaflet support member 64 can extend across a portion of the free edges 28 and 26 of the posterior and anterior mitral leaflets 22 and 20.

Figure 14A:
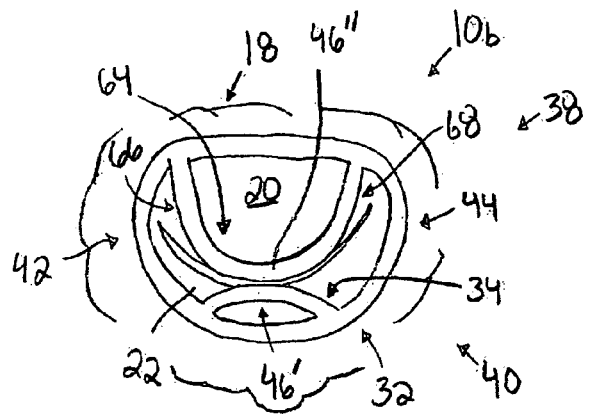
FIG. 14A is a plan view showing an alternative embodiment of the apparatus in FIG. 1A.
Figure 14B:
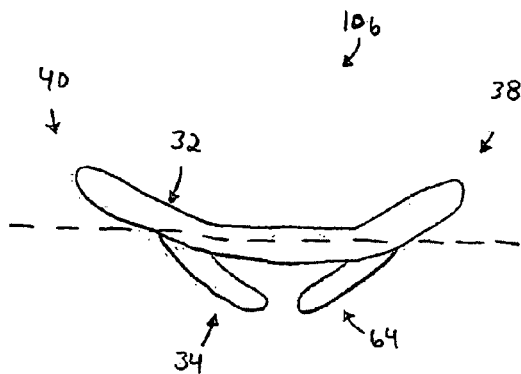
FIG. 14B is a side view of the apparatus in FIG. 14A.

Another embodiment of the present invention is illustrated in FIGS. 14A-B. The apparatus $10_b$ shown in FIGS. 14A-B is identically constructed as the apparatus 10 and $10_a$ shown in FIGS. 1A-E and FIGS. 10A-B, except as described below. In FIGS. 14A-B, structures that are identical as structures in FIGS. 1A-E and FIGS. 10A-B use the same reference numbers, whereas structures that are similar but not identical carry the suffix "b". It should be appreciated that the apparatus $10_b$ can be constructed from any of the materials described above, and that the apparatus can include a layer 52 of biocompatible material and/or a therapeutic agent(s), as also described above.

The apparatus $10_b$ can comprise an annular support member 32, at least one posterior leaflet support member 34, and at least one anterior leaflet support member 64. The annular support member 32, the posterior leaflet support member 34, and the anterior leaflet support member 64 can be identically or similarly constructed as the annular support member described above. As shown in FIG. 14A, for example, the apparatus $10_b$ can include a posterior leaflet support member 34 comprising a first arcuate center portion 46' integrally formed with and extending between first and second end portions 48 and 50. Each of the first arcuate center portion 46', the first end portion 48, and the second end portion 50 can have a convex shape relative to the anterior end portion 38 of the annular support member 32. The first and second end portions 48 and 50 can be securely connected to the anterior end portion 38 at oppositely disposed locations.

The apparatus 10$_b$ can also include an anterior leaflet support member 64 comprising a second arcuate center portion 46" integrally formed with and extending between third and fourth end portions 66 and 68. Each of the second arcuate center portion 46", the third end portion 66, and the fourth end portion 68 can have a concave shape relative to the anterior end portion 38 of the annular support member 32. The third and fourth end portions 66 and 68 can be securely connected to the anterior end portion 38 at oppositely disposed locations. As shown in FIG. 14B, each of the anterior and posterior leaflet support members 64 and 34 extend below the longitudinal axis 36 of the annular support member 32 and facilitate proper coaptation of the anterior and posterior mitral leaflets 20 and 22, respectively.

Figure 15:
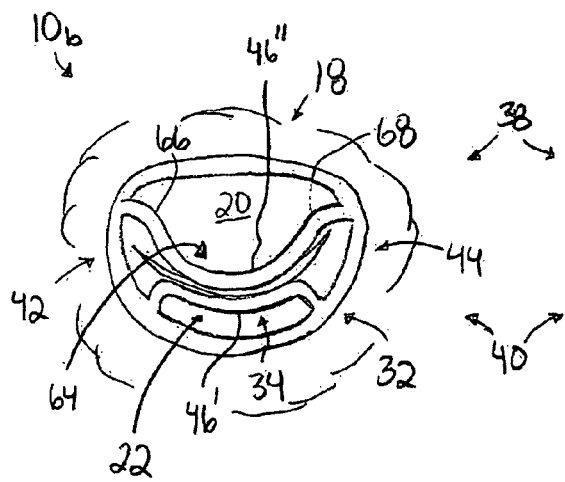
FIG. 15 is a plan view showing an alternative embodiment of the apparatus in FIG. 14A.

FIGS. 15-18 illustrate other geometric variations of the apparatus 10$_b$ shown in FIGS. 14A-B. As shown in FIG. 15, for example, the posterior leaflet support member 34 can include a first arcuate center portion 46' integrally formed with and extending between first and second end portions 48 and 50. The first arcuate center portion 46' can have a convex shape relative to the anterior end portion 38 of the annular support member 32. Each of the first and second end portions 48 and 50 can also have a concave shape relative to the anterior end portion 38. The first and second end portions 48 and 50 can be securely connected to the posterior end portion 40 at oppositely disposed locations. The posterior leaflet support member 34 can extend across a portion of the free edge 28 of the posterior leaflet 22.

The anterior leaflet support member 64 of the apparatus 10$_b$ can include a second arcuate center portion 46" integrally formed with and extending between third and fourth end portions 66 and 68. The second arcuate center portion 46" can have a convex shape relative to the anterior end portion 38 of the annular support member 32. Each of the third and fourth end portions 66 and 68 can have a concave shape relative to the anterior end portion 38. The third and fourth end portions 66 and 68 can be securely connected to the first and second intermediate portions 42 and 44, respectively. The anterior leaflet support member 64 can extend across a portion of the free edge 26 of the anterior leaflet 20.

Figure 16:
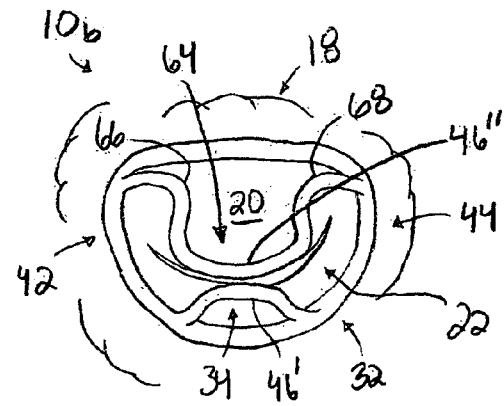
FIG. 16 is a plan view showing an alternative embodiment of the apparatus in FIG. 14A.

As shown in FIG. 16, the posterior leaflet support member 34 of the apparatus 10$_b$ can alternatively comprise a first arcuate center portion 46' integrally formed with an extending between first and second end portions 48 and 50. The first arcuate center portion 46' can have a concave shape relative to the anterior end portion 38 of the annular support member 32. Each of the first and second end portions 48 and 50 can have a convex shape relative to the anterior end portion 38. The first and second end portions 48 and 50 can be securely connected to the posterior end portion 40 at oppositely disposed locations. The posterior leaflet support member 34 can extend across a portion of the free edge 28 of the posterior leaflet 22.

The anterior leaflet support member 64 of the apparatus 10$_b$ can alternatively comprise a second arcuate center portion 46" integrally formed with and extending between third and fourth end portions 66 and 68. The second arcuate center portion 46" can have a convex shape relative to the anterior end portion 38 of the annular support member 32. Each of the third and fourth end portions 66 and 68 can have a concave shape relative to the anterior end portion 38. The third and fourth end portions 66 and 68 can be securely connected to the first and second intermediate portions 42 and 44, respectively. The anterior leaflet support member 64 can extend across a portion of the free edge 26 of the anterior leaflet 20.

Figure 17:
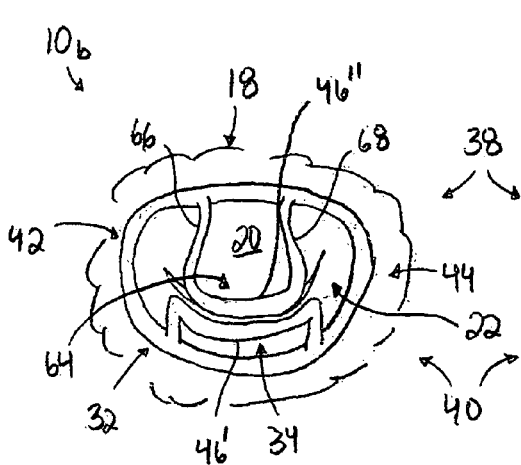
FIG. 17 is a plan view showing an alternative embodiment of the apparatus in FIG. 14A.

As shown in FIG. 17, the apparatus 10$_b$ can alternatively include a posterior leaflet support member 34 comprising a first arcuate center portion 46' integrally formed with and extending between first and second end portions 48 and 50. The first arcuate center portion 46' can have a convex shape relative to the anterior end portion 38 of the annular support member 32. Each of the first and second end portions 48 and 50 can extend substantially perpendicular to the anterior end portion 38 of the annular support member 32. Additionally, each of the first and second end portions 48 and 50 can be securely attached to the posterior end portion 40 at oppositely disposed locations.

The apparatus 10$_b$ can additionally include an anterior leaflet support member 64 having a U-shaped configuration and comprising a second arcuate center portion 46" integrally formed with and extending between third and fourth end portions 66 and 68. The second arcuate center portion 46" can have a convex shape relative to the anterior end portion 38 of the annular support member 32. Each of the third and fourth end portions 66 and 68 can have a convex shape relative to the first and second intermediate portions 42 and 44, respectively. Additionally, each of the third and fourth end portions 66 and 68 can be securely connected to the anterior end portion 38 of the annular support member 32 at oppositely disposed locations.

Figure 18:
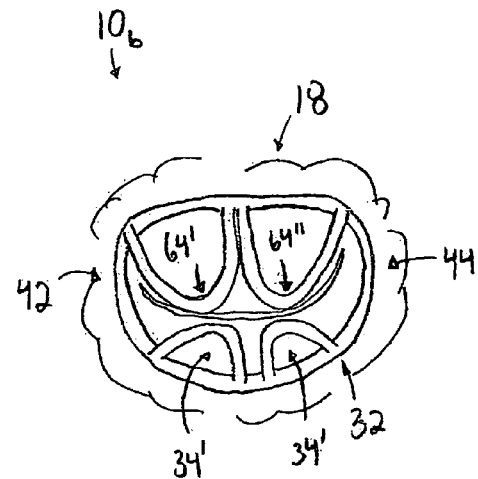
FIG. 18 is a plan view showing an alternative embodiment of the apparatus in FIG. 14A.

As shown in FIG. 18, the apparatus 10$_b$ can alternatively comprise first and second posterior leaflet support members 34' and 34" oppositely disposed from first and second anterior leaflet support members 64' and 64". Each of the first and second anterior leaflet support members 64' and 64" can comprise a first arcuate center portion 46', a third end portion 66, and a fourth end portion 68. Each of the first arcuate center portion 46', the third end portion 66, and the fourth end portion 68 can have a convex shape relative to the anterior end portion 38 of the annular support member 32. Each of the first and second posterior leaflet support members 34' and 34" can include a second arcuate center portion 46" integrally formed with and extending between first and second end portions 48 and 50. The first and second end portions 48 and 50 of the first posterior leaflet support members 34' can be securely connected to the first intermediate portion 42 and the posterior end portion 40 of the annular support member 32, respectively. Additionally, the first and second end portions 48 and 50 of the second posterior leaflet support member 34" can be securely connected to the posterior end portion 40 and the second intermediate portion 44 of the annular support member 32, respectively. Each of the second arcuate center portion 46", the first end portion 48, and the second end portion 50 can have a concave shape relative to the anterior end portion 38 of the annular support member 32.

Figure 19A:
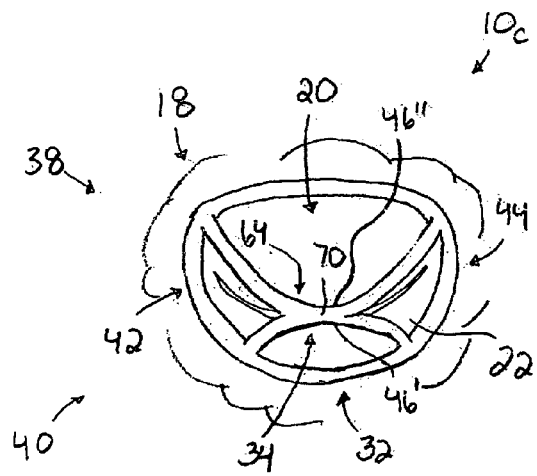
FIG. 19A is a plan view showing an alternative embodiment of the apparatus in FIG. 14A.
Figure 19B:
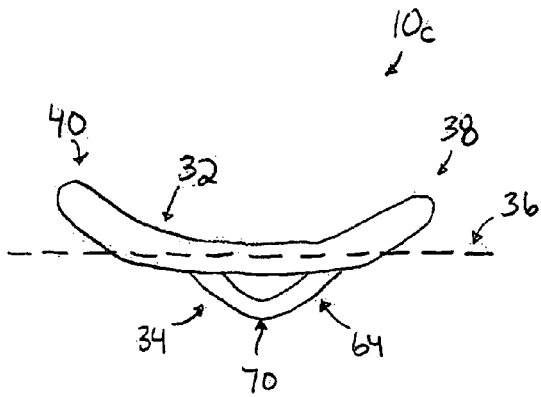
FIG. 19B is a side view of the apparatus in FIG. 19A.

Another embodiment of the present invention is illustrated in FIGS. 19A-B. The apparatus 10$_c$ shown in FIGS. 19A-B is identically constructed as the apparatus 10$_b$ shown in FIGS. 14A-B, except as described below. In FIGS. 19A-B, structures that are identical as structures in FIGS. 14A-B use the same reference numbers, whereas structures that are similar but not identical carry the suffix "c". It should be appreciated that the apparatus 10$_c$ can be constructed from any of the materials described above, and that the apparatus can include a layer 52 of biocompatible material and/or a therapeutic agent(s), as also described above.

The apparatus 10$_c$ can comprise an annular support member 32, at least one posterior leaflet support member 34, and at least one anterior leaflet support member 64. The annular support member 32, the posterior leaflet support member 34, and the anterior leaflet support member 64 can be identically or similarly constructed as the annular support member described above. As shown in FIG. 19A, for example, the apparatus 10$_c$ can include a posterior leaflet support member 34 comprising a first arcuate center portion 46' integrally formed with and extending between first and second end portions 48 and 50. Each of the first arcuate center portion 46', the first end portion 48, and the second end portion 50 can have a concave shape relative to the anterior end portion 38 of the annular support member 32. The first and second end portions 48 and 50 can be securely connected to the posterior end portion 40 at oppositely disposed locations.

The apparatus 10$_c$ can also include an anterior leaflet support member 64 comprising a second arcuate center portion 46" integrally formed with and extending between third and fourth end portions 66 and 68. Each of the second arcuate center portion 46", the third end portion 66, and the fourth end portion 68 can have a convex shape relative to the anterior end portion 38 of the annular support member 32. The third and fourth end portions 66 and 68 can be securely connected to the first and second intermediate portions 42 and 44, respectively. As shown in FIGS. 19A-B, the first and second arcuate center portions 46' and 46" can be joined together to form a common junction 70. The first and second arcuate center portions 46' and 46" can be integrally formed or, alternatively, only in physical contact with one another but not integrally formed therewith. The common junction 70 can extend below the longitudinal axis 36 of the annular support member 32 to facilitate proper coaptation of the anterior and posterior mitral leaflets 20 and 22 by supporting a portion of each of the free edges 26 and 28 of the anterior and posterior mitral valve leaflets.

Figures 20, 21:
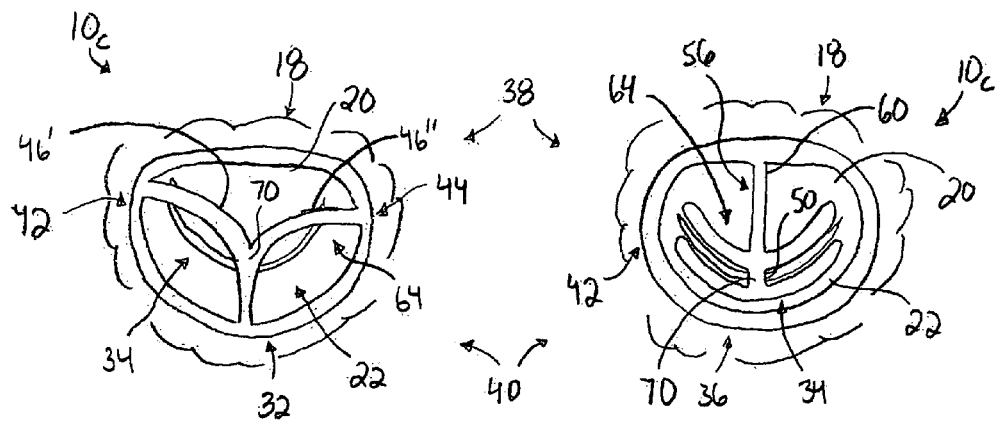
FIG. 20 is a plan view showing an alternative embodiment of the apparatus in FIG. 19A.
FIG. 21 is a plan view showing an alternative embodiment of the apparatus in FIG. 19A.
Figures 22, 23:
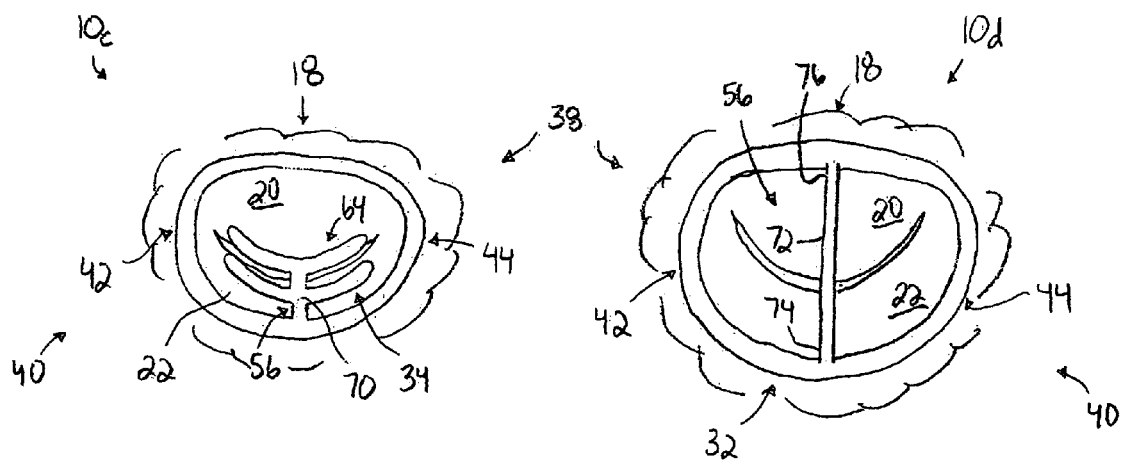
FIG. 22 is a plan view showing an alternative embodiment of the apparatus in FIG. 19A.
FIG. 23 is a plan view showing an alternative embodiment of the apparatus in FIG. 1A.

FIGS. 20-22 illustrate other geometric variations of the apparatus 10$_c$ shown in FIGS. 19A-B. As shown in FIG. 20, for example, the anterior leaflet support member 64, the posterior leaflet support member 34, and the common junction 70 can have a Y-shaped configuration and be securely connected to the annular support member 32. The anterior leaflet support member 64 can comprise a first arcuate center portion 46' integrally formed with and extending between first and second end portions 48 and 50. Each of the first arcuate center portion 46', the first end portion 48, and the second end portion 50 can have a convex shape relative to the first intermediate portion 42. The first and second end portions 48 and 50 can be securely connected to the first intermediate portion 42 and the posterior end portion 40, respectively.

The posterior leaflet support member 34 can comprise a second arcuate center portion 46" integrally formed with and extending between third and fourth end portions 66 and 68. Each of the second arcuate center portion 46", the third end portion 66, and the fourth end portion 68 can have a convex shape relative to the second intermediate portion 44. The third and fourth end portions 66 and 68 can be securely connected to the second intermediate portion 44 and the posterior end portion 40, respectively. Additionally, the first and second arcuate center portions 46' and 46" can be joined together to form a common junction 70 that extends below the longitudinal axis 36 of the annular support member 32 and supports a portion of each of the free edges 26 and 28 of the anterior and posterior mitral valve leaflets 20 and 22.

As shown in FIG. 21, each of the posterior and anterior leaflet support members 34 and 64 can include first and second arcuate center portions 46' and 46", respectively, having a convex shape relative to the anterior end portion 38 of the annular support member 32. The anterior and posterior leaflet support members 64 and 34 can be joined together and integrally formed with a first brace member 56 having first and second ends 58 and 60 and extending substantially perpendicular to the anterior and posterior leaflet support members. The first end 58 of the first brace member 56 can form a common junction 70 that extends across a portion of the free edges 26 and 28 of the anterior and posterior mitral leaflets 20 and 22. The second end 60 of the first brace member 56 can be securely connected to the anterior end portion 38 of the annular support member 32.

As shown in FIG. 22, each of the posterior and anterior leaflet support members 34 and 64 can include first and second arcuate center portions 46' and 46", respectively, having a convex shape relative to the anterior end portion 38 of the annular support member 32. The anterior and posterior leaflet support members 64 and 34 can be joined together and integrally formed with a first brace member 56 having first and second ends 58 and 60 and extending substantially perpendicular to the anterior and posterior leaflet support members. The first end 58 of the first brace member 56 can form a common junction 70 that extends across a portion of the free edges 26 and 28 of the anterior and posterior mitral leaflets 20 and 22. The second end 60 of the first brace member 56 can be securely connected to the posterior end portion 40 of the annular support member 32.

Figures 26, 27:
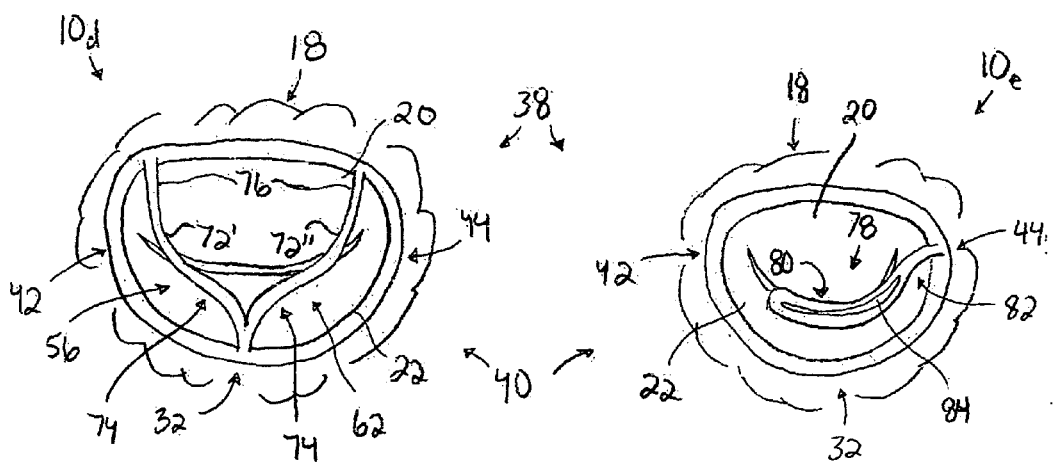
FIG. 26 is a plan view showing an alternative embodiment of the apparatus in FIG. 25.
FIG. 27 is a plan view showing an alternative embodiment of the apparatus in FIG. 1A.

Another embodiment of the present invention is illustrated in FIGS. 23 26. The apparatus 10$_d$ shown in FIGS. 23-26 are identically constructed as the apparatus 10 shown in FIGS. 1A-E, except as described below. In FIGS. 23-26, structures that are identical as structures in FIGS. 1A-E use the same reference numbers, whereas structures that are similar but not identical carry the suffix "d". It should be appreciated that the apparatus 10$_d$ can be constructed from any of the materials described above, and that the apparatus can include a layer 52 of biocompatible material and/or a therapeutic agent(s), as also described above.

The apparatus 10$_d$ can comprise an annular support member 32 and a first brace member 56 securely connected thereto. As shown in FIG. 23, the apparatus 10$_d$ can comprise a first brace member 56 having a rod-like configuration and including a middle portion 72 extending between first and second end portions 74 and 76. The first and second end portions 74 and 76 can be securely attached to the posterior and anterior end portions 40 and 38 of the annular support member 32, respectively. The middle portion 72 can extend across both the anterior and posterior mitral valve leaflets 26 and 28 and thereby provide support for a portion of the free edges of the anterior and posterior valve leaflets 20 and 22.

Figures 24, 25:
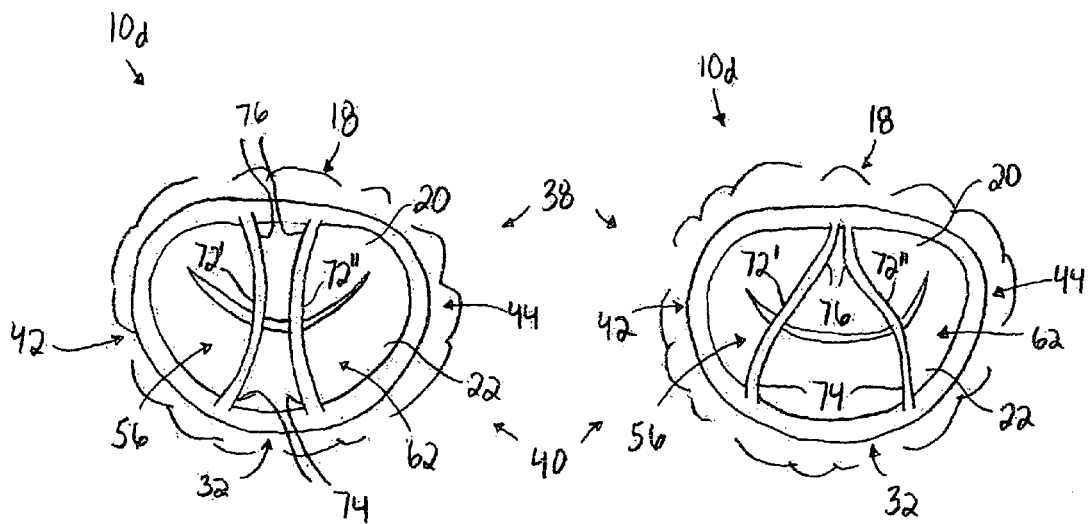
FIG. 24 is a plan view showing an alternative embodiment of the apparatus in FIG. 23.
FIG. 25 is a plan view showing an alternative embodiment of the apparatus in FIG. 24.

As shown in FIG. 24, the apparatus 10$_d$ can alternatively comprise an annular support member 32 and first and second brace members 56 and 62 securely connected thereto. Each of the first and second brace members 56 and 62 can have a rod-like configuration and include first and second middle portions 72' and 72", respectively, extending between first and second end portions 74 and 76 and having an arcuate shape. Each of the first and second middle portions 72' and 72" has a concave shape relative to the first and second intermediate portions 42 and 44 of the annular support member 32, respectively. The first and second middle portions 72' and 72" can extend across both the anterior and posterior mitral valve leaflets 20 and 22 and thereby provide support for a portion of the free edges 26 and 28 of the leaflets. The first end portion 74 of each of the first and second brace members 56 and 62 can be securely attached to the posterior end portion 40 of the annular support member 32. The second end portion 76 of the each of the first and second brace members 56 and 62 can be securely attached to the anterior end portion 38 of the annular support member 38.

As shown in FIG. 25, the apparatus 10$_d$ can alternatively comprise an annular support member 32 and first and second brace members 56 and 62 securely connected thereto. Each of the first and second brace members 56 and 62 can have a curvilinear configuration and include first and second middle portions 72' and 72", respectively, extending between first and second end portions 74 and 76. Each of the first and second middle portions 72' and 72" has a substantially linear shape relative to the first and second end portions 74 and 76. The first and second middle portions 72' and 72" can extend across both the anterior and posterior mitral valve leaflets 20 and 22 and thereby provide support for a portion of the free edges 26 and 28 of the leaflets. The first end portion 74 of the first brace member 56 and the second end portion 76 of the second brace member 62 can each have a concave shape relative to the second intermediate portion 44 of the annular support member 32. The second end portion 76 of the first brace member 56 and the first end portion 74 of the second brace member 62 can each have a convex shape relative to the second intermediate portion 44 of the annular support member 32. The first end portion 74 of each of the first and second brace members 56 and 62 can be securely connected to the first and second intermediate portions 42 and 44, respectively. Additionally, the second end portion 76 of each of the first and second brace members 56 and 62 can be securely connected to the anterior end portion 38 of the annular support member 32.

As shown in FIG. 26, the apparatus 10$_d$ can alternatively comprise an annular support member 32 and first and second brace members 56 and 62 securely connected thereto. Each of the first and second brace members 56 and 62 can have a curvilinear configuration and include first and second middle portions 72' and 72", respectively, extending between first and second end portions 74 and 76. Each of the first and second middle portions 72' and 72" has a substantially linear shape relative to the first and second end portions 74 and 76. The first and second middle portions 72' and 72" can extend across both the anterior and posterior mitral valve leaflets 20 and 22 and thereby provide support for a portion of the free edges 26 and 28 of the leaflets. The first end portion 74 of the first brace member 56 and the second end portion 76 of the second brace member 62 can each have a convex shape relative to the second intermediate portion 44 of the annular support member 32. The second end portion 76 of the first brace member 56 and the first end portion 74 of the second brace member 62 can each have a concave shape relative to the second intermediate portion 44 of the annular support member 32. The second end portion 76 of each of the first and second brace members 56 and 62 can be securely connected to the first and second intermediate portions 42 and 44, respectively. Additionally, the first end portion 74 of each of the first and second brace members 56 and 62 can be securely connected to the anterior end portion 38 of the annular support member 32.

Another embodiment of the present invention is illustrated in FIGS. 27-30B. The apparatus 10$_e$ shown in FIGS. 27-30B are identically constructed as the apparatus 10 shown in FIGS. 1A-E, except as described below. In FIGS. 27-30B, structures that are identical as structures in FIGS. 1A-E use the same reference numbers, whereas structures that are similar but not identical carry the suffix "e". It should be appreciated that the apparatus 10$_e$ can be constructed from any of the materials described above, and that the apparatus can include a layer 52 of biocompatible material and/or a therapeutic agent(s), as also described above.

Figure 28:
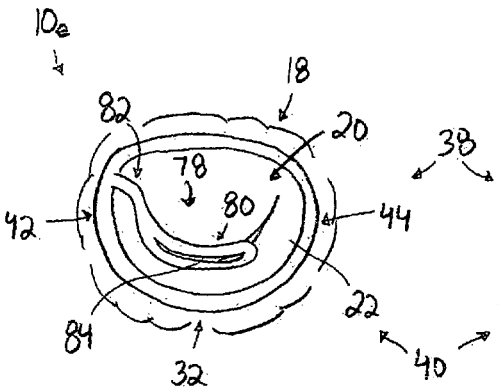
FIG. 28 is a plan view showing an alternative embodiment of the apparatus in FIG. 27.
Figure 29A:
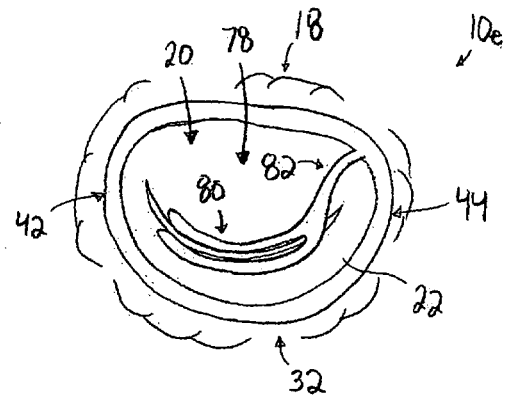
FIG. 29A is a plan view showing an alternative embodiment of the apparatus shown in FIG. 27.
Figure 29B:
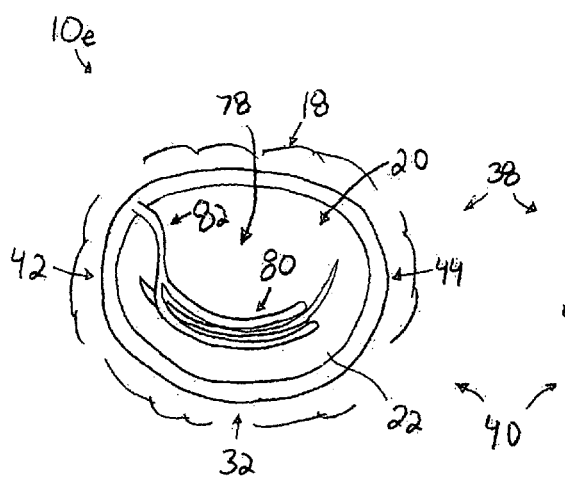
FIG. 29B is a plan view showing an alternative embodiment of the apparatus in FIG. 27.

The apparatus 10$_e$ can comprise an annular support member 32 and a leaflet support member 78 securely connected thereto. The leaflet support member 78 can comprise a coaptation portion 80 integrally formed with an attachment portion 82. As shown in FIGS. 27-28, the coaptation portion 80 can have an arcuate, loop-shaped configuration and include an aperture 84 to facilitate blood flow through the coaptation portion. Alternatively, the coaptation portion 80 can have a fork-like configuration (FIGS. 29A-B). The coaptation portion 80 can extend across all or only a portion of the free edges 26 and 28 of the anterior and posterior mitral leaflets 20 and 22. The attachment portion 82 of the leaflet support member 78 can be securely connected to the second intermediate portion 44 (FIG. 27 and FIG. 29A) or the first intermediate portion 42 (FIG. 28 and FIG. 29B) of the annular support member 32.

Figure 30A:
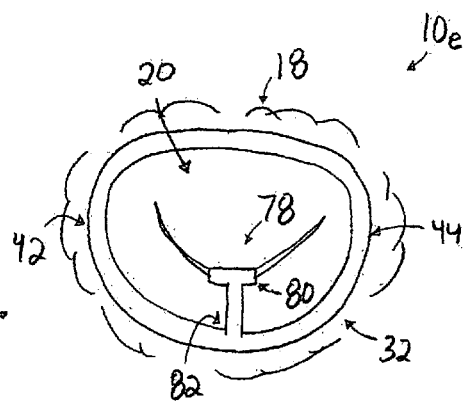
FIG. 30A is a plan view showing an alternative embodiment of the apparatus in FIG. 27.
Figure 30B:
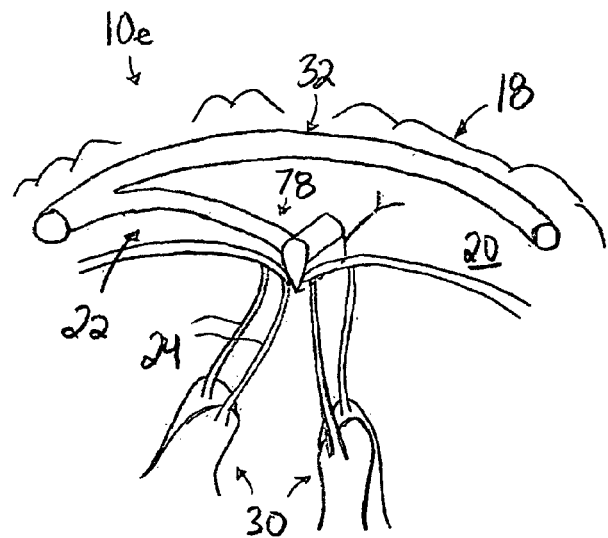
FIG. 30B is a cross-sectional view showing the apparatus in FIG. 30A implanted in a heart valve.

As shown in FIGS. 30A-B, the coaptation portion 80 can alternatively have a wing-like configuration. It will be appreciated that the coaptation portion 80 can have a variety of configurations including, for example, a spherical configuration (not shown), an ellipsoidal configuration (not shown), a disk-shaped configuration (not shown), or a sheet-like configuration (not shown). As also shown in FIGS. 30A-B, the attachment portion 82 of the leaflet support member 78 can be securely attached to the posterior end portion 40 of the annular support member 32.

The particular position selected to implant the coaptation portion 80 may depend on a variety of factors, such as the condition of a patient's heart, including the valve leaflets 20 and 22, the delivery technique utilized to implant the apparatus 10$_e$, the type of leaflet support member 78 utilized to treat the valve 12, and other similar factors, such as the geometry (e.g., size and shape) of the valve. For instance, the coaptation portion 80 may be positioned between the valve leaflets 20 and 22 (FIG. 30B), below the free edges 26 and 28 of the valve leaflets, or at a level of the valve annulus 18 so that the coaptation portion permits the valve 12 to close during systole and thereby prevent or mitigate regurgitant of blood flow through the valve.

Figure 31:
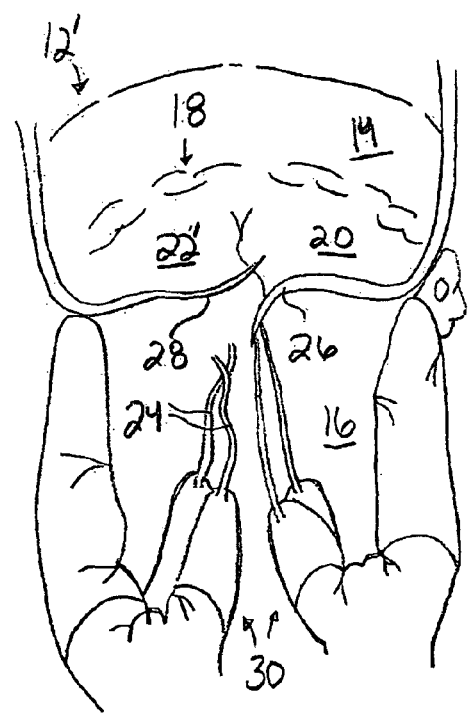
FIG. 31 is a cross-sectional view showing a prolapsed posterior mitral valve leaflet.

Another embodiment of the present invention is illustrated in FIGS. 31-38. As shown in FIGS. 31-38, a method is provided for treating regurgitation of blood flow through a diseased heart valve, such as a regurgitant mitral valve 12' (FIG. 31). Although the method of the present invention will be described below using the apparatus 10 shown in FIG. 32, it should be appreciated that any of the apparatus described above may also be used to treat regurgitation of blood flow through a diseased heart valve. Additionally, it should be appreciated that any of the apparatus described above may also be used to treat a prolapsed anterior mitral valve leaflet (not shown), as well as a prolapsed tricuspid leaflet (not shown).

One step of the method includes providing an apparatus 10 (FIG. 32) for treating regurgitation of blood flow through the diseased mitral valve 12'. As shown in FIG. 32, the apparatus 10 is similarly constructed as the apparatus in FIGS. 1A-E. For example, the apparatus 10 comprises an annular support member 32 and a posterior leaflet support member 34 securely connected thereto. The annular support member 32 defines a longitudinal axis 36 (as described above) and includes an anterior end portion 38, a posterior end portion 40, and oppositely disposed first and second intermediate portions 42 and 44 extending between the anterior and posterior end portions.

The posterior leaflet support member 34 is integrally formed with and extends between the first and second intermediate portions 42 and 44 of the annular support member 32. As shown in FIG. 32, the posterior leaflet support member 34 comprises an arcuate center portion 46 integrally formed with and extending between first and second end portions 48 and 50. The arcuate center portion 46 has a convex shape relative to the anterior end portion 38 of the annular support member 32. The first and second end portions 48 and 50 are securely connected to the first and second intermediate portions 42 and 44 of the annular support member 32, respectively.

Figure 33D:
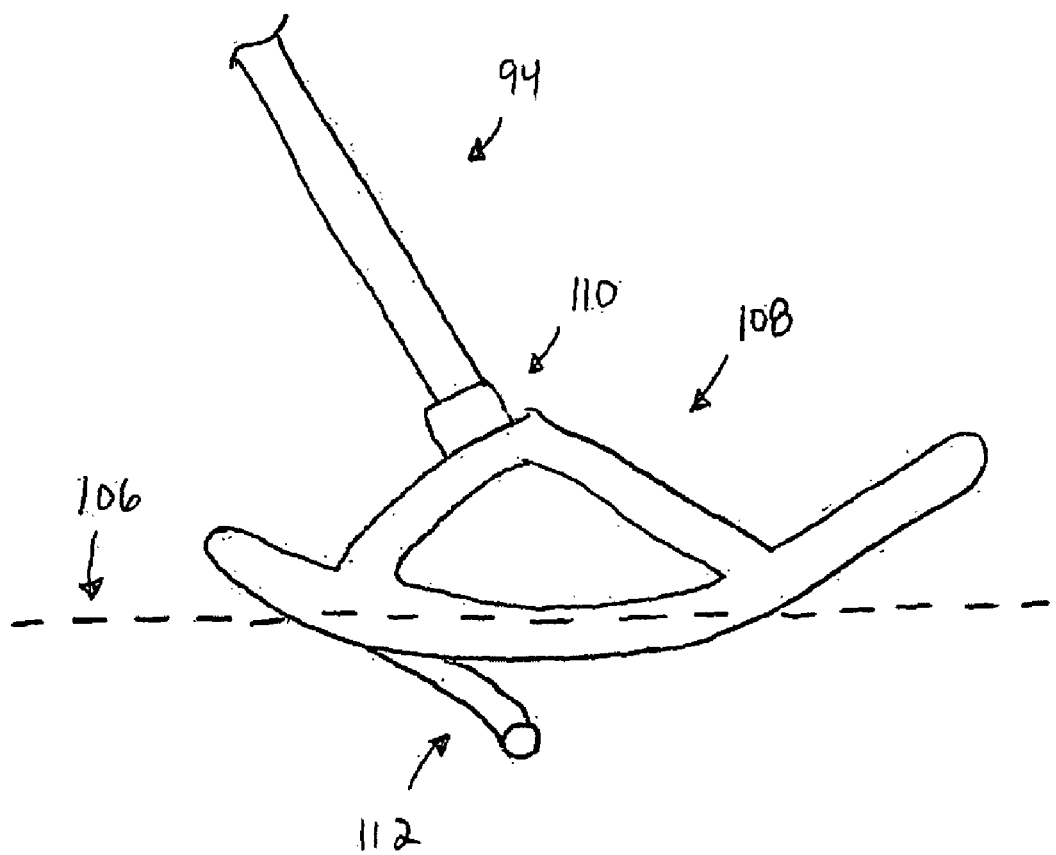
FIG. 33D is a side view showing an alternative embodiment of the handle member in FIG. 33C.

To treat the regurgitant mitral valve 12', the dimensions of the valve are first obtained to determine optimal dimensions for the apparatus 10. Sizing of the mitral valve 12' is performed using the sizing device 86 illustrated in FIGS. 33A-D. As shown in FIG. 33A, the sizing device 86 comprises a handle member 88 securely attached to a sizing member 90. The handle member 88 includes a handle 92 fluidly connected to a distal attachment portion 94. The handle 92 is for guiding the sizing device 86, and the distal attachment portion 94 is for connecting the handle to the sizing member 90.

Referring to FIG. 33B, the sizing member 90 includes an annular support member 96 having an anterior end portion 98, a posterior end portion 100, and first and second oppositely disposed intermediate portions 102 and 104 extending between the anterior and posterior end portions. The annular support member 96 has a planar configuration (FIG. 33C); however, it should be appreciated that the annular support member can have a 3D or saddle-shaped configuration as shown in FIG. 33D.

The sizing member 90 defines a longitudinal axis 106 (FIG. 33C) and includes a bracing portion 108 having an attachment mechanism 110, such as an aperture for mating to the distal attachment portion 94 of the handle member 88. As shown in FIG. 33C, the bracing portion 108 extends above the longitudinal axis 106 of the annular support member 96. The sizing member 90 further includes a leaflet support member 112 for supporting a heart valve leaflet, such as a prolapsed mitral leaflet 22'. As shown in FIG. 33C, the leaflet support member 112 extends below the longitudinal axis 106 of the annular support member 96.

Figure 34:
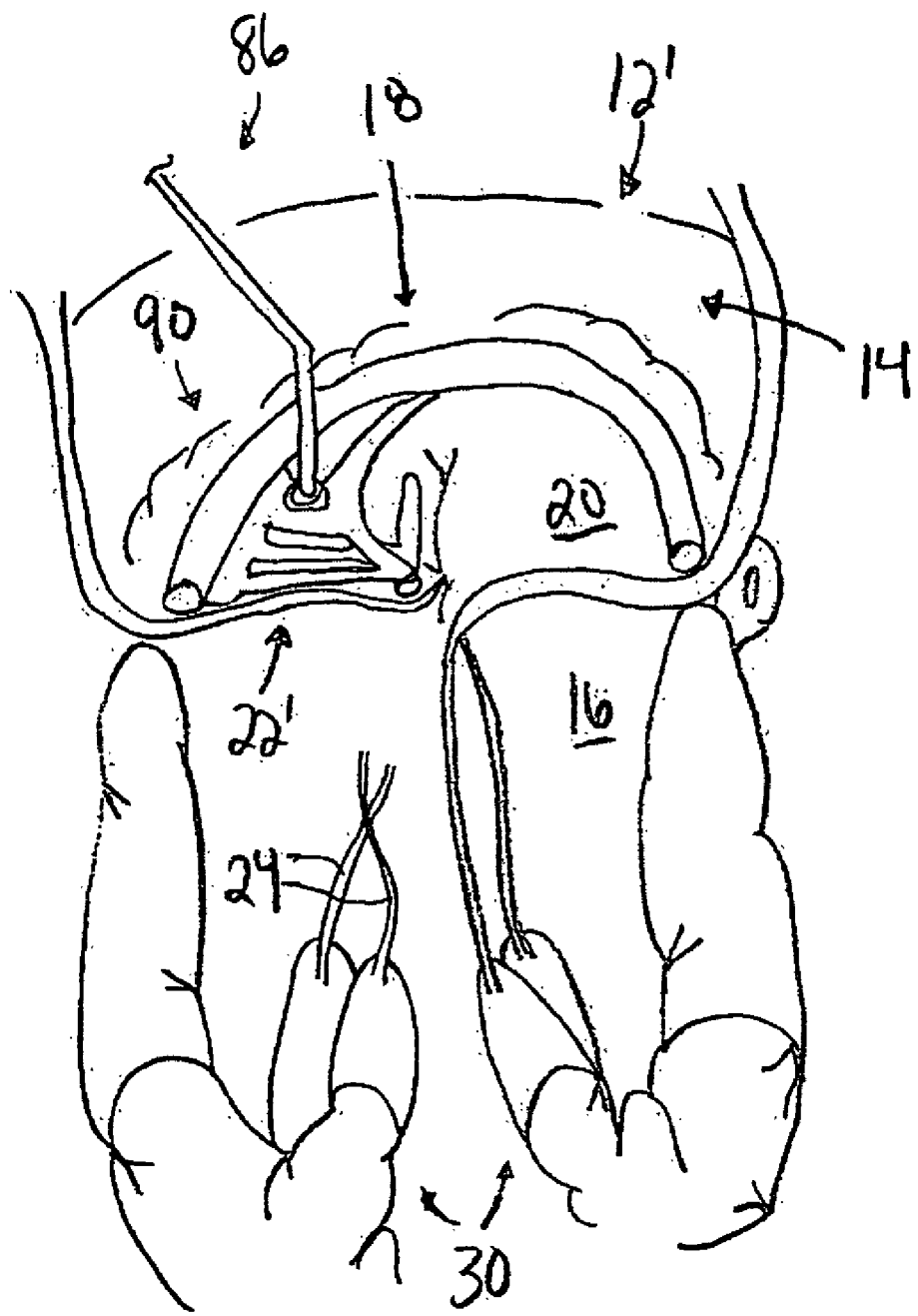
FIG. 34 is a perspective view showing the sizing device in FIGS. 33A-D deployed in the left atrium.

To determine the dimensions of the mitral valve 12' using the sizing device 86, access to the mitral valve is gained via an open-chest surgical procedure. During the procedure, the mitral valve 12' is visualized so that the sizing device 86, and in particular the sizing member 90, can be positioned about a superior aspect of the mitral valve. Using the handle 92 to guide the sizing member 90 into the left atrium 14, the sizing device 86 is positioned about the mitral valve 12' so that the annular support member 96 contacts the mitral valve annulus 18 and the leaflet support member 112 contacts the free edge 28 of the posterior mitral valve leaflet 22' (FIG. 34).

Next, blood flow through the mitral valve 12' is monitored to assess coaptation between the leaflet support member 112 and the mitral valve leaflet 22'. Differently dimensioned sizing members 90 can be placed over the mitral valve 12' until substantially normal blood flow through the mitral valve is observed. "Normal blood flow" can refer to the movement of blood through a mammalian valve or vasculature that is unimpeded and progresses under physiologically-normal pressures and at a physiologically-normal rate. When substantially normal blood flow is observed through the mitral valve 12', the dimensions of the sizing member 90 are noted and an apparatus 10 having dimensions that correspond to the dimensions of the sizing member is selected for implantation. It should be appreciated that a saline solution test may additionally or alternatively be used to assess fluid flow and proper leaflet 22' coaptation through the mitral valve 12'.

Figure 35:
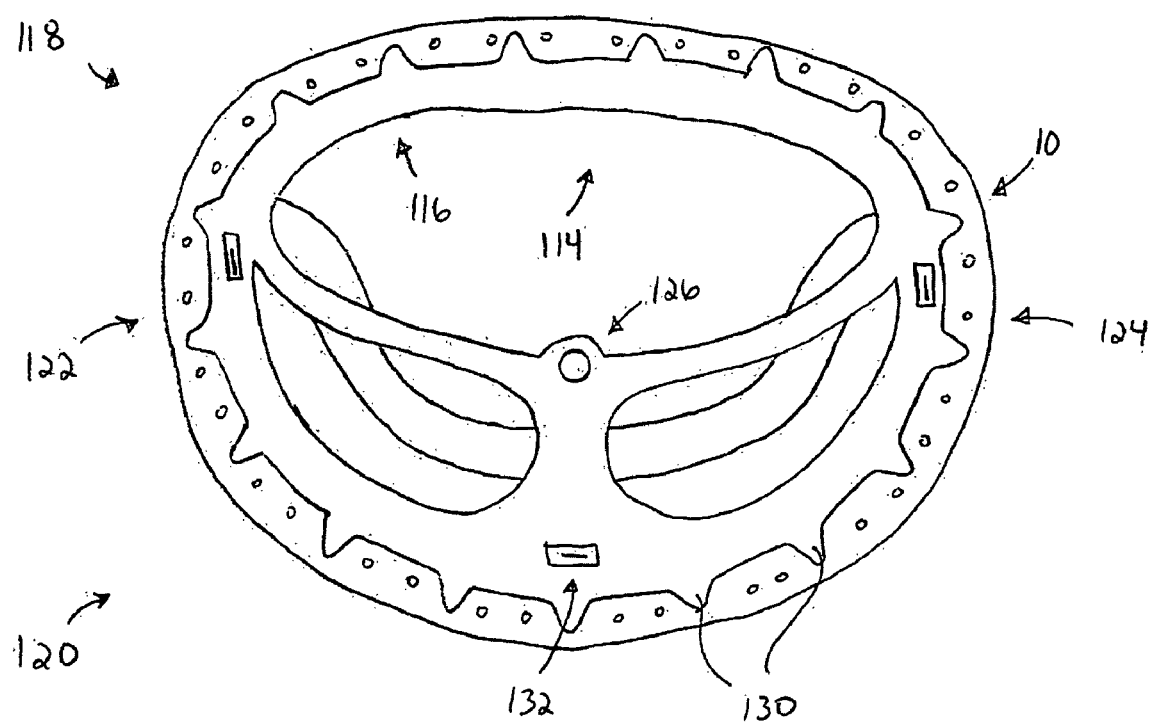
FIG. 35 is a top view showing the apparatus in FIG. 32 coupled to the sizing member of the delivery device.
Figure 36:
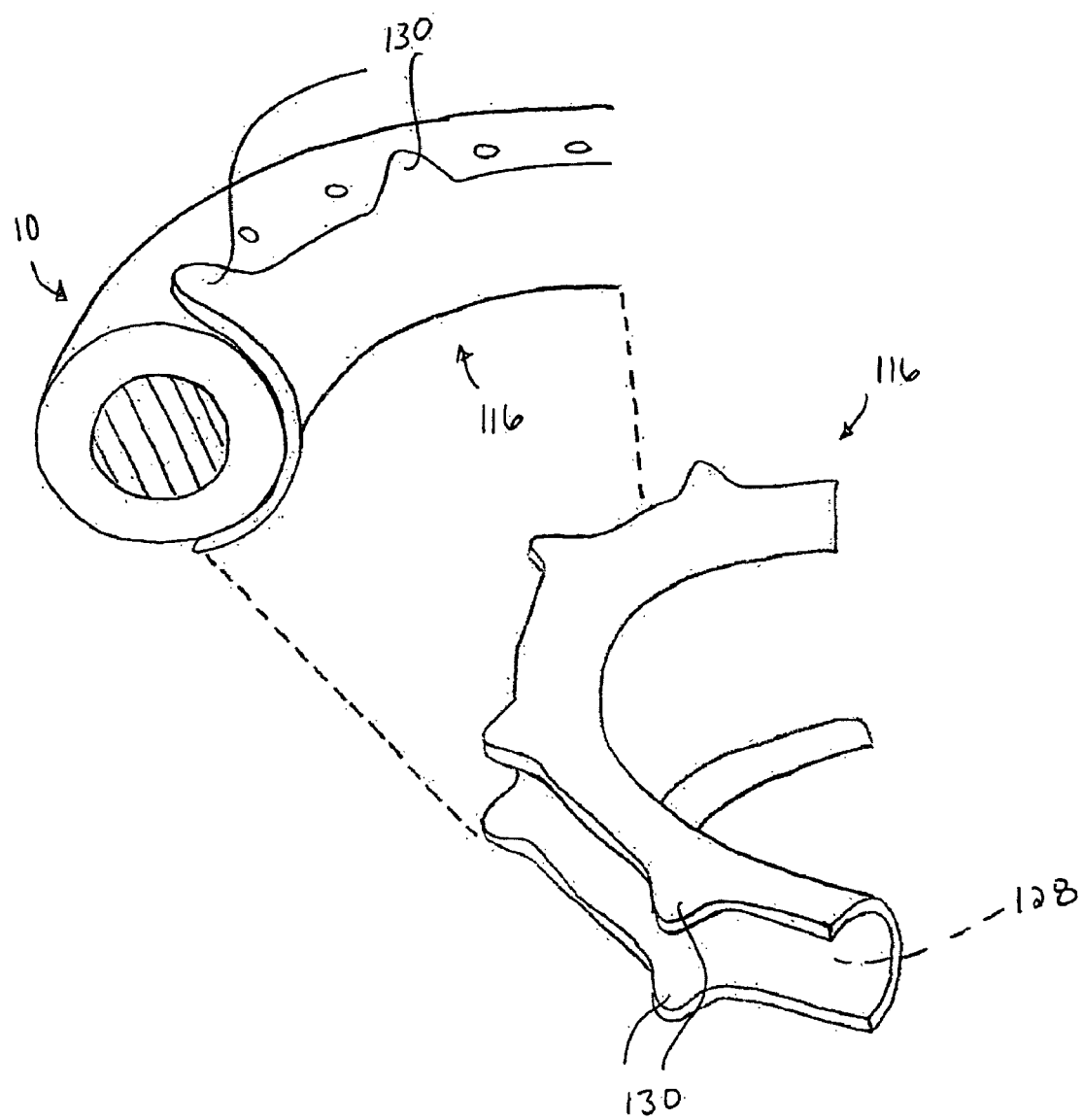
FIG. 36 is a magnified perspective view showing a portion of the delivery device being coupled to the apparatus in FIG. 35.

After selecting an appropriately-dimensioned apparatus 10, the apparatus is attached to a delivery device 114 (FIGS. 35-36). As shown in FIG. 35, the delivery device 114 comprises a ring-shaped support member 116 having an anterior end portion 118, a posterior end portion 120, and oppositely disposed first and second intermediate portions 122 and 124 extending between the anterior and posterior end portions. The delivery device 114 includes an attachment mechanism 126, such as an aperture for connecting to the distal attachment portion 94 of the sizing device 86. The ring-shaped support member 116 has a C-shaped cross-section that defines a channel 128 (FIG. 36). The channel 128 extends around the periphery of the ring-shaped support member 116 and includes a plurality of extensions 130 to facilitate attachment of the apparatus 10 to the delivery device 114. The delivery device 114 also includes a plurality of suture attachment points 132 through which sutures can be threaded to attach the apparatus 10 to the delivery device.

Figure 37:
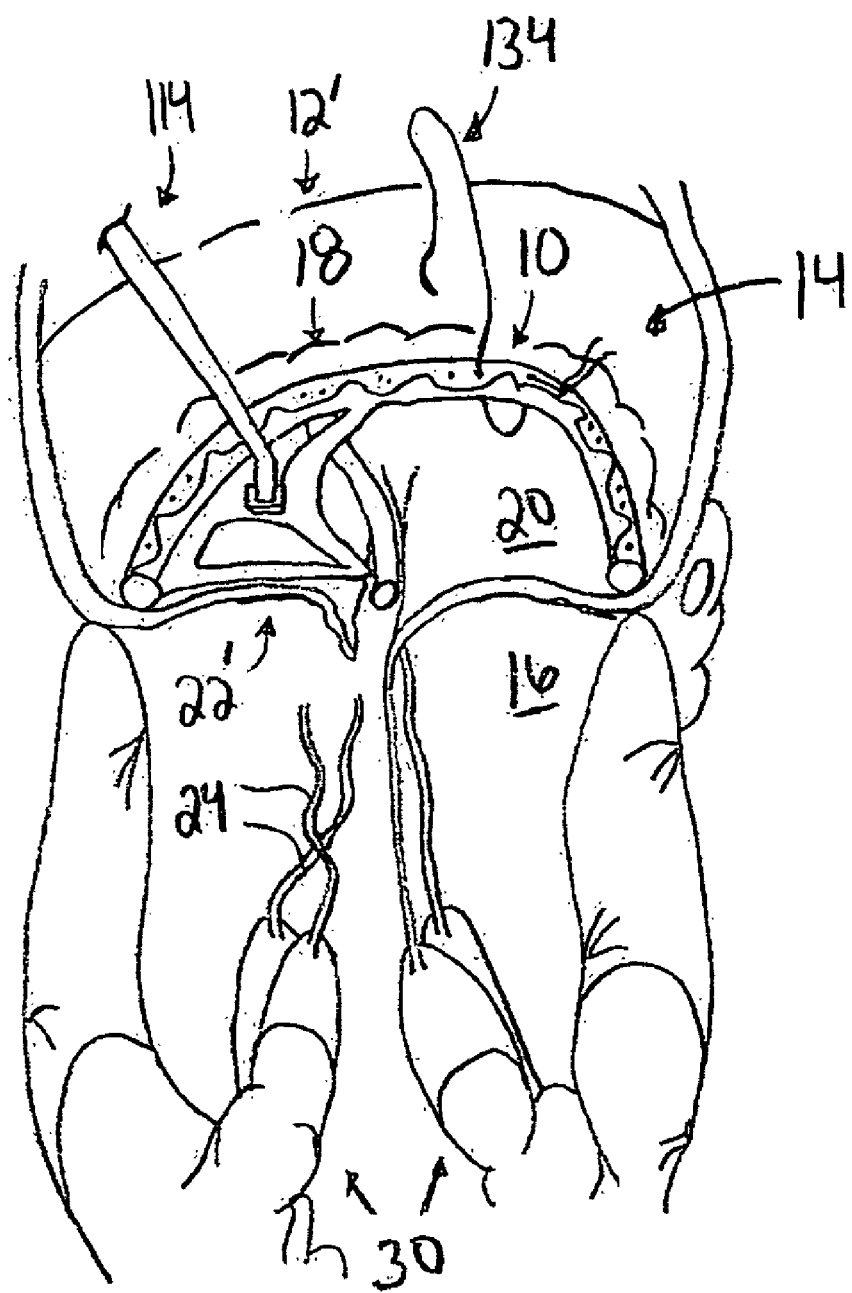
FIG. 37 is a cross-sectional view showing the apparatus in FIG. 36 being delivered to the mitral valve.
Figure 38:
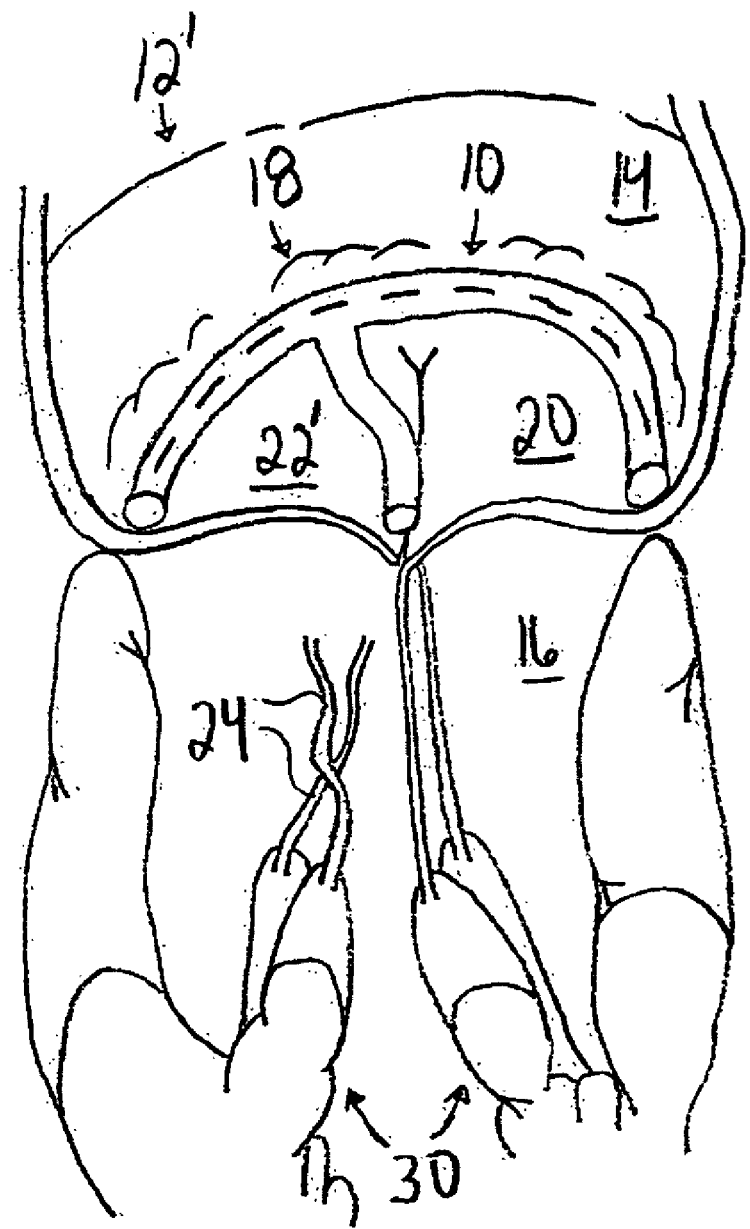
FIG. 38 is a cross-sectional view showing the apparatus in FIG. 32 securely attached to the mitral valve.

Once the apparatus 10 is securely attached to the delivery device 114 (FIG. 35), sutures 134 are placed in the mitral annulus 18. The delivery device 114 is then positioned about the superior aspect of the mitral valve 12' (FIG. 37). Next, the sutures 134 are pulled through the markers 54 (e.g., holes) while the delivery device 114 engages the mitral valve 12' and the annular support member 32 of the apparatus 10 is pressed against the mitral annulus 18. The sutures 134 are then tightened so that the apparatus 10 is securely positioned about the mitral valve 12'. After tightening of the sutures 134 is complete, the sutures are cut so that the delivery device 114 is detached from the apparatus 10 and removed from the left atrium 14. With the apparatus 10 securely in place (FIG. 38), the posterior leaflet support member 34 supports the free edge 28 of the posterior mitral leaflet 22' during systole and thereby prevents or mitigates prolapse of the posterior mitral leaflet.

From the above description of the invention, those skilled in the art will perceive improvements, changes and modifications. Such improvements, changes, and modifications are within the skill of the art and are intended to be covered by the appended claims.

Having described the invention, I claim:

1. An apparatus for treating regurgitation of blood flow through a diseased heart valve, the diseased heart valve including an annulus, an anterior valve leaflet, and a posterior valve leaflet, each of the anterior and posterior valve leaflets having a free edge, said apparatus comprising:

an annular support member having an anterior end portion, a posterior end portion, and oppositely disposed first and second intermediate portions extending between said anterior and posterior end portions, said anterior end portion and said posterior end portion of said annular support member being dimensioned for attachment to anterior and posterior portions of the annulus of the heart valve, respectively, said posterior end portion and said first and second intermediate portions forming a continuous arc so that said posterior end portion has a convex shape relative to said anterior end portion; and at least one arc-shaped posterior leaflet support member securely connected to said annular support member and being dimensioned to extend across a portion of the free edge of the posterior valve leaflet;

said posterior leaflet support member comprising a center portion integrally formed with and extending between first and second end portions, said first end portion, said second end portion, and said center portion forming a continuous arc so that said posterior leaflet support member has a concave shape relative to said anterior end portion, at least one of said first and second end portions being securely attached to said posterior end portion;

wherein said annular support member has a saddle-shaped configuration and at least a portion of said posterior leaflet support member extends beyond said annular support member so that said at least a portion of said posterior leaflet support member is positioned below the annulus of the diseased heart valve when said apparatus is implanted thereon.

2. The apparatus of claim 1, wherein said first and second end portions of said posterior leaflet support member are securely attached to said first intermediate portion and said posterior end portion of said annular support member, respectively.

3. The apparatus of claim 1, wherein said first and second end portions of said posterior leaflet support member are securely attached to said posterior end portion and said second intermediate portion of said annular support member, respectively.

4. The apparatus of claim 1, wherein each of said first and second end portions of said posterior leaflet support member has a concave shape relative to said anterior end portion of said annular support member.

5. The apparatus of claim 1, wherein each of said first and second end portion of said posterior leaflet support member has a convex shape relative to said anterior end portion of said annular support member.

6. The apparatus of claim 1, wherein said first and second end portions of said posterior leaflet support member is securely attached to said posterior end portion at oppositely disposed locations.

7. The apparatus of claim 1 further comprising:
at least one anterior leaflet support member securely connected to said annular support member and being dimensioned to extend across a portion of the free edge of the anterior valve leaflet, said anterior leaflet support member comprising a second arcuate center portion integrally formed with and extending between third and fourth end portions, said second arcuate center portion having a convex shape relative to said anterior end portion, each of said third and fourth end portions having a convex shape relative to said anterior end portion and being securely attached to said annular support member at oppositely disposed locations.

8. The apparatus of claim 1 further comprising:
a first posterior leaflet support member securely connected to said annular support member and being dimensioned to extend across a portion of the free edge of the posterior valve leaflet, said first posterior leaflet support member comprising a first arcuate center portion integrally formed with and extending between first and second end portions, said first arcuate center portion having a concave shape relative to said anterior end portion, said first and second end portions being securely connected to said first intermediate portion and said posterior end portion, respectively; and
a second posterior leaflet support member securely connected to said annular support member and being dimensioned to extend across a portion of the free edge of the posterior valve leaflet, said second posterior leaflet support member comprising a second arcuate center portion integrally formed with and extending between third and fourth end portions, said second arcuate center portion having a concave shape relative to said anterior end portion, said third and fourth end portions being securely connected to said posterior end portion and said second intermediate portion, respectively.

9. The apparatus of claim 1, wherein each of said annular support member and said posterior leaflet support member has a three-dimensional (3D) shape that corresponds to the 3D shape of the annulus and the posterior valve leaflet, respectively.

10. The apparatus of claim 1, wherein said posterior leaflet support member includes an adjustment mechanism for selectively adjusting the position of said posterior leaflet support member relative to said annular support member.

11. The apparatus of claim 1, wherein said posterior leaflet support member has a semi-rigid configuration so that said posterior leaflet support member is bendable to various positions relative to said annular support member.

12. An apparatus for treating regurgitation of blood flow through a diseased heart valve, the diseased heart valve including an annulus, an anterior valve leaflet, and a posterior valve leaflet, each of the anterior and posterior valve leaflets having a free edge, said apparatus consisting of:
an annular support member having an anterior end portion, a posterior end portion, and oppositely disposed first and second intermediate portions extending between said anterior and posterior end portions, said annular support member being dimensioned for attachment to the annulus of the heart valve, said posterior end portion and said first and second intermediate portions forming a continuous arc so that said posterior end portion has a convex shape relative to said anterior end portion; and
at least one arc-shaped posterior leaflet support member securely connected to said annular support member and being dimensioned to extend across a portion of the free edge of the posterior valve leaflet;
said posterior leaflet support member comprising an arcuate center portion integrally formed with and extending between first and second end portions, said first end portion, said second end portion, and said arcuate center portion forming a continuous arc so that said posterior leaflet support member has a concave shape relative to said anterior end portion, at least one of said first and second end portions being securely attached to said posterior end portion.

13. An apparatus for treating regurgitation of blood flow through a diseased mitral valve, the diseased mitral valve including a D-shaped annulus, an anterior mitral leaflet, and a posterior mitral leaflet, each of the anterior and posterior mitral leaflets having a free edge, said apparatus comprising:
an annular support member having an anterior end portion, a posterior end portion, and oppositely disposed first and second intermediate portions extending between said anterior and posterior end portions, said annular support member having a D-shaped configuration that corresponds to the D-shaped mitral valve annulus, said anterior and posterior end portions of said annular support member being dimensioned for attachment to the anterior and posterior portions of the mitral annulus, respectively, said posterior end portion and said first and second intermediate portions forming a continuous arc so that said posterior end portion has a convex shape relative to said anterior end portion; and
at least one arc-shaped posterior leaflet support member securely connected to said annular support member and being dimensioned to extend across a portion of the free edge of the posterior mitral leaflet;
said posterior leaflet support member comprising a center portion integrally formed with and extending between first and second end portions, said first end portion, said second end portion, and said center portion forming a continuous arc so that said posterior leaflet support member has a concave shape relative to said anterior end portion, at least one of said first and second end portions being securely attached to said posterior end portion;
wherein said annular support member has a saddle-shaped configuration and at least a portion of said posterior leaflet support member extends beyond said annular support member so that said at least a portion of said posterior leaflet support member is positioned below the annulus of the diseased heart valve when said apparatus is implanted thereon.

14. The apparatus of claim 13, wherein said at least one posterior leaflet support member is dimensioned to extend across only a portion of the free edge of the posterior mitral leaflet.

* * * * *